US010768173B1

(12) United States Patent
Arslan et al.

(10) Patent No.: US 10,768,173 B1
(45) Date of Patent: Sep. 8, 2020

(54) MULTIVALENT BINDING COMPOSITION FOR NUCLEIC ACID ANALYSIS

(71) Applicant: Element Biosciences, Inc., San Diego, CA (US)

(72) Inventors: Sinan Arslan, San Diego, CA (US); Molly He, San Diego, CA (US); Matthew Kellinger, San Diego, CA (US); Jake Levieux, San Diego, CA (US); Michael Previte, San Diego, CA (US); Junhua Zhao, San Diego, CA (US); Su Zhang, Rosemead, CA (US)

(73) Assignee: ELEMENT BIOSCIENCES, INC., San Diego, CA (US)

( * ) Notice: Subject to any disclaimer, the term of this patent is extended or adjusted under 35 U.S.C. 154(b) by 0 days.

(21) Appl. No.: 16/579,794

(22) Filed: Sep. 23, 2019

Related U.S. Application Data

(60) Provisional application No. 62/897,172, filed on Sep. 6, 2019.

(51) Int. Cl.
| | |
|---|---|
| *C12Q 1/6869* | (2018.01) |
| *C07H 21/00* | (2006.01) |
| *G01N 33/53* | (2006.01) |
| *G01N 33/58* | (2006.01) |
| *C12Q 1/6874* | (2018.01) |

(52) U.S. Cl.
CPC ....... *G01N 33/5308* (2013.01); *C12Q 1/6874* (2013.01); *G01N 33/582* (2013.01)

(58) Field of Classification Search
CPC ........ C12Q 1/68; C07H 21/00; G01N 33/582; G01N 33/5308
See application file for complete search history.

(56) References Cited

U.S. PATENT DOCUMENTS

| | | | |
|---|---|---|---|
| 3,950,649 A | 4/1976 | Yonekubo | |
| 4,222,743 A | 9/1980 | Wang | |
| 5,184,021 A | 2/1993 | Smith | |
| 5,422,712 A | 6/1995 | Ogino | |
| 5,695,936 A * | 12/1997 | Mandrand | C08G 81/02 435/6.12 |
| 6,287,766 B1 * | 9/2001 | Nolan | C12Q 1/6816 435/6.12 |
| 6,440,748 B1 | 8/2002 | Katerkamp et al. | |
| 6,482,590 B1 | 11/2002 | Ullman et al. | |
| 6,548,607 B2 | 4/2003 | Halverson et al. | |
| 6,664,079 B2 * | 12/2003 | Ju | C12Q 1/6872 435/91.1 |
| 6,818,425 B2 | 11/2004 | Hjorleifsdottir et al. | |
| 6,829,051 B2 | 12/2004 | Abe et al. | |
| 6,833,246 B2 | 12/2004 | Balasubramanian | |
| 7,030,383 B2 | 4/2006 | Babayoff et al. | |
| 7,169,560 B2 | 1/2007 | Lapidus et al. | |
| 7,264,934 B2 | 9/2007 | Fuller | |
| 7,416,844 B2 | 8/2008 | Korlach et al. | |
| 7,755,841 B2 | 7/2010 | Christenson et al. | |
| 7,960,116 B2 | 6/2011 | Eid et al. | |
| 8,039,817 B2 | 10/2011 | Feng et al. | |
| 8,120,002 B2 | 2/2012 | Van Dijk et al. | |
| 8,133,672 B2 | 3/2012 | Bjornson et al. | |
| 8,143,599 B2 | 3/2012 | Feng et al. | |
| 8,242,463 B2 | 8/2012 | Feng et al. | |
| 8,257,954 B2 | 9/2012 | Clark et al. | |
| 8,278,630 B1 | 10/2012 | Feng et al. | |
| 8,367,813 B2 | 2/2013 | Korlach | |
| 8,399,196 B2 | 3/2013 | Hoser | |
| 8,405,048 B2 | 3/2013 | Hayashi | |
| 8,481,264 B2 | 7/2013 | Bjornson et al. | |
| 8,530,164 B2 | 9/2013 | Patel et al. | |
| 8,546,772 B2 | 10/2013 | Feng et al. | |
| 8,580,539 B2 | 11/2013 | Korlach | |
| 8,586,947 B1 | 11/2013 | Feng et al. | |
| 8,592,148 B2 | 11/2013 | Williams et al. | |
| 8,632,975 B2 | 1/2014 | Vander Horn et al. | |
| 8,658,365 B2 | 2/2014 | Bjornson et al. | |
| 8,698,102 B2 | 4/2014 | Feng et al. | |
| 8,703,461 B2 | 4/2014 | Peris et al. | |
| 8,715,932 B2 | 5/2014 | Su et al. | |
| 9,068,220 B2 | 6/2015 | Feng et al. | |

(Continued)

FOREIGN PATENT DOCUMENTS

| | | |
|---|---|---|
| WO | WO-2006065266 A2 | 6/2006 |
| WO | WO-2007061425 A1 | 5/2007 |

(Continued)

OTHER PUBLICATIONS

Batra et al., Structure 14:757 (Year: 2006).*
Ju et al.,Four-color DNA sequencing by synthesis using ceavable fluorescent nucleotide reversible terminators. PNAS 103(52) :19635-19640 (Year: 2006).*
Ju et al., Supporting Text for PNAS 103(52): 19,635 (Year: 2006).*
Mardis, E.., Next-generation DNA Sequencing Methods. Annual Reviews in Genomics Human Genetics 9 :387 (Year: 2008).*

(Continued)

*Primary Examiner* — Ethan C Whisenant

(74) *Attorney, Agent, or Firm* — Wilson Sonsini Goodrich & Rosati

(57) ABSTRACT

Multivalent binding compositions including a particle-nucleotide conjugate having a plurality of copies of a nucleotide attached to the particle are described. The multivalent binding compositions allow one to localize detectable signals to active regions of biochemical interaction, e.g., sites of protein-protein interaction, protein-nucleic acid interaction, nucleic acid hybridization, or enzymatic reaction, and can be used to identify sites of base incorporation in elongating nucleic acid chains during polymerase reactions and to provide improved base discrimination for sequencing and array based applications.

30 Claims, 15 Drawing Sheets

(11 of 15 Drawing Sheet(s) Filed in Color)

(56) References Cited

U.S. PATENT DOCUMENTS

| | | | |
|---|---|---|---|
| 9,255,258 | B2 | 2/2016 | Vander Horn et al. |
| 9,365,898 | B2 | 6/2016 | Feng et al. |
| 9,399,767 | B2 | 7/2016 | Peris et al. |
| 9,546,398 | B2 | 1/2017 | Peter et al. |
| 9,593,315 | B2 | 3/2017 | Peris et al. |
| 9,605,310 | B2 | 3/2017 | Balasubramanian et al. |
| 9,765,310 | B2 | 9/2017 | Vander Horn et al. |
| 9,932,631 | B1 | 4/2018 | Dambacher et al. |
| 9,951,385 | B1 | 4/2018 | Vijayan et al. |
| 9,957,291 | B2 | 5/2018 | Sebo et al. |
| 10,077,470 | B2 | 9/2018 | Vijayan et al. |
| 10,253,352 | B2 | 4/2019 | Nguyen et al. |
| 10,294,514 | B2 | 5/2019 | Iyidogan et al. |
| 10,300,452 | B2 | 5/2019 | Sun et al. |
| 10,336,991 | B2 | 7/2019 | Peris et al. |
| 10,400,272 | B1 | 9/2019 | Middleton et al. |
| 10,415,029 | B2 | 9/2019 | Dambacher et al. |
| 10,428,378 | B2 | 10/2019 | Iyidogan et al. |
| 10,443,098 | B2 | 10/2019 | Vijayan et al. |
| 10,501,796 | B2 | 12/2019 | Buermann et al. |
| 10,519,496 | B2 | 12/2019 | Balasubramanian et al. |
| 10,584,379 | B2 | 3/2020 | Vijayan et al. |
| 10,597,643 | B2 | 3/2020 | Iyidogan et al. |
| 2001/0031483 | A1* | 10/2001 | Sorge .................. C12N 15/10 435/41 |
| 2002/0030811 | A1 | 3/2002 | Schindler |
| 2002/0139936 | A1 | 10/2002 | Dumas |
| 2003/0152490 | A1 | 8/2003 | Trulson et al. |
| 2008/0160580 | A1* | 7/2008 | Adessi ................ C12Q 1/6837 435/91.1 |
| 2010/0137143 | A1 | 6/2010 | Rothberg et al. |
| 2010/0311144 | A1 | 12/2010 | Peris et al. |
| 2011/0039259 | A1* | 2/2011 | Ju ...................... C12Q 1/6869 435/6.12 |
| 2011/0301044 | A1 | 12/2011 | Feng et al. |
| 2012/0322666 | A1* | 12/2012 | Pham .................. C12Q 1/6869 506/2 |
| 2015/0362458 | A1* | 12/2015 | Yanagawa .......... G01N 27/4145 506/13 |
| 2017/0145495 | A1 | 5/2017 | Sebo et al. |
| 2017/0145496 | A1 | 5/2017 | Sebo et al. |
| 2017/0189444 | A1 | 7/2017 | Ismagilov et al. |
| 2017/0191125 | A1 | 7/2017 | Vijayan et al. |
| 2017/0369857 | A1 | 12/2017 | Vander Horn et al. |
| 2018/0023108 | A1* | 1/2018 | Chen ...................... C12P 19/34 435/91.2 |
| 2018/0080073 | A1* | 3/2018 | Vijayan .................. C12P 19/34 |
| 2018/0187245 | A1 | 7/2018 | Dambacher et al. |
| 2018/0195099 | A1* | 7/2018 | Kranz ..................... C12P 19/34 |
| 2018/0208983 | A1 | 7/2018 | Dambacher et al. |
| 2018/0237847 | A1* | 8/2018 | Culler .................... A61K 35/66 |
| 2018/0280975 | A1 | 10/2018 | Kilcoin et al. |
| 2018/0346507 | A1 | 12/2018 | Sebo et al. |
| 2018/0360974 | A1 | 12/2018 | Kwiatkowski et al. |
| 2019/0048404 | A1 | 2/2019 | Dambacher |
| 2019/0119740 | A1 | 4/2019 | Ahn et al. |
| 2019/0119742 | A1 | 4/2019 | Zhang et al. |
| 2019/0241945 | A1 | 8/2019 | Malyshev et al. |
| 2019/0338352 | A1 | 11/2019 | Nemiroski et al. |
| 2019/0367974 | A1 | 12/2019 | Fleischer et al. |
| 2020/0010885 | A1 | 1/2020 | Malyshev et al. |
| 2020/0032317 | A1 | 1/2020 | Rohrman et al. |
| 2020/0087637 | A1 | 3/2020 | Iyidogan |

FOREIGN PATENT DOCUMENTS

| | | |
|---|---|---|
| WO | WO-2010016937 A2 | 2/2010 |
| WO | WO-2017007774 A1 | 1/2017 |
| WO | WO-2017014762 A1 | 1/2017 |
| WO | WO-2017117235 A1 | 7/2017 |
| WO | WO-2019018366 A1 | 1/2019 |

OTHER PUBLICATIONS

Heather et al. The Sequence of Sequencers: The History of Sequencing DNA. Genomics 107:1-8 (2016).

* cited by examiner

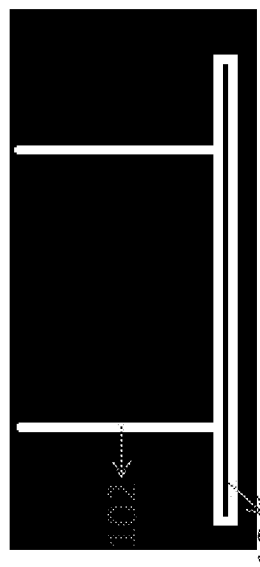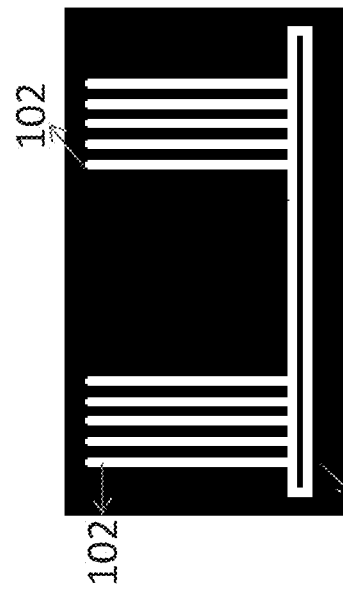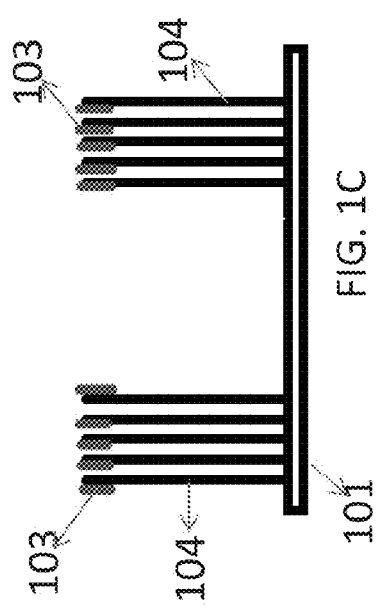

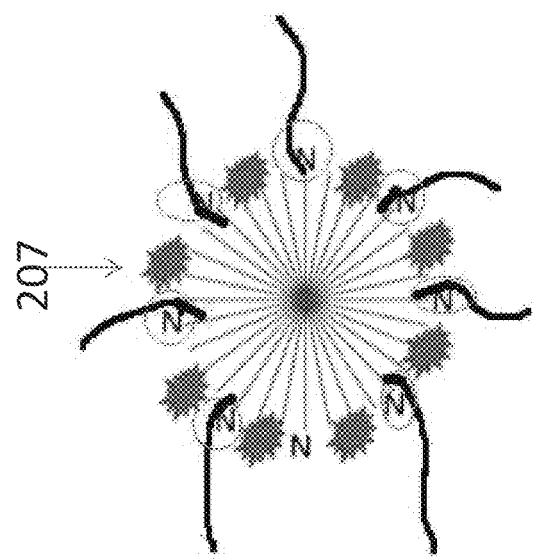
FIG. 2B
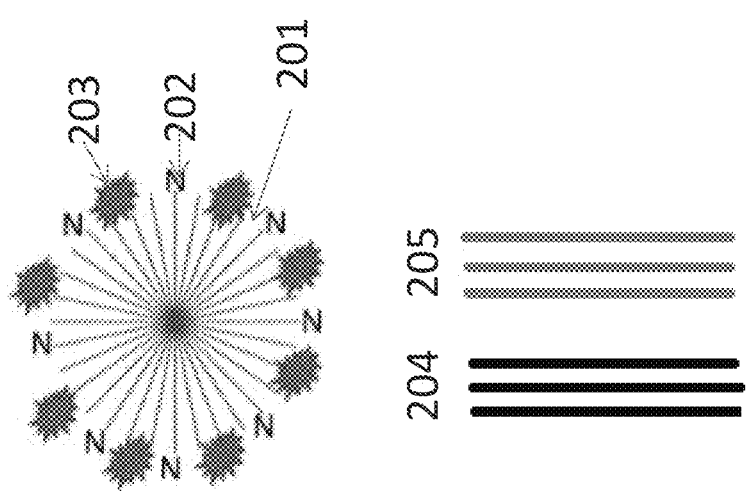
FIG. 2A

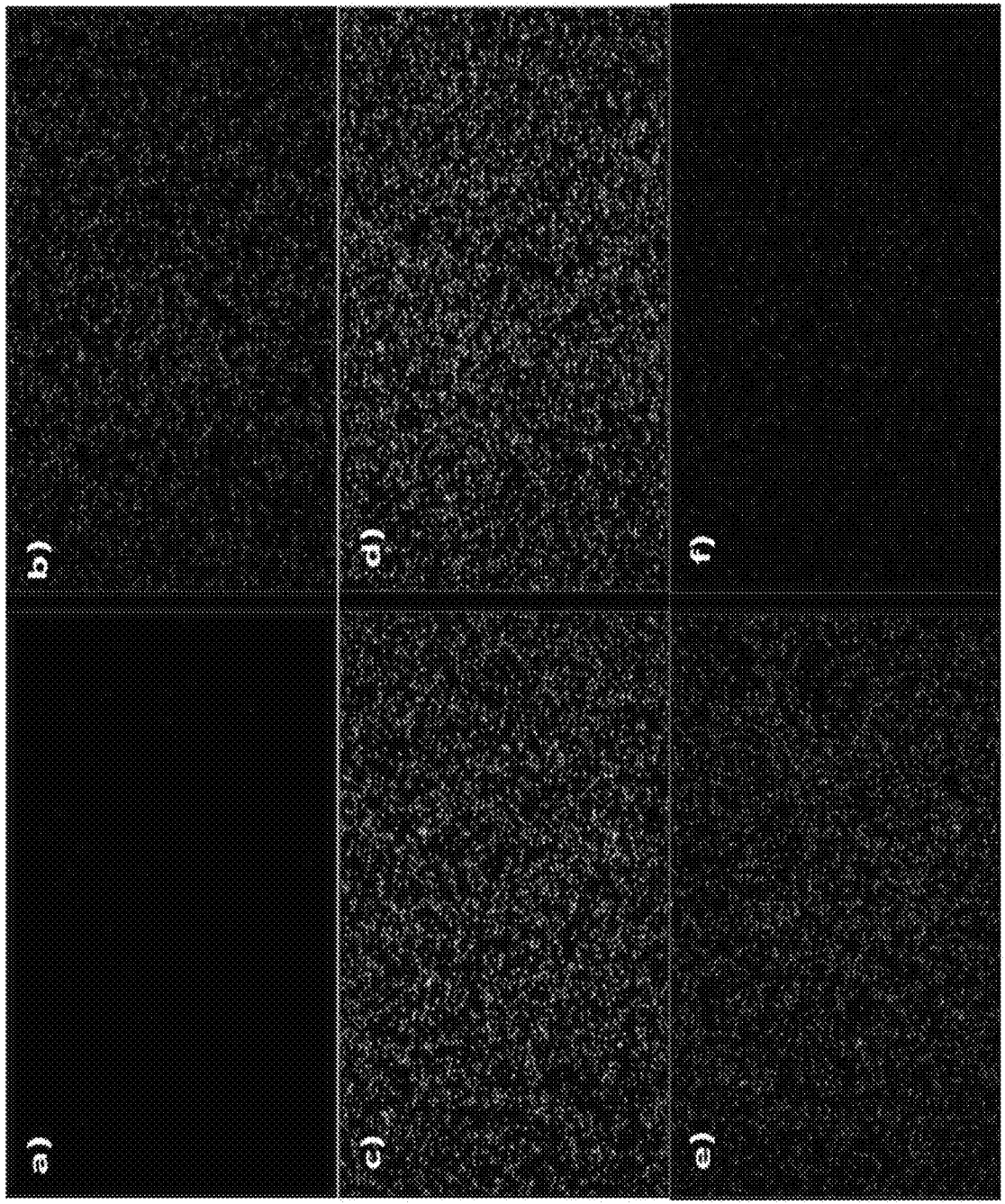
FIGS. 7A-F

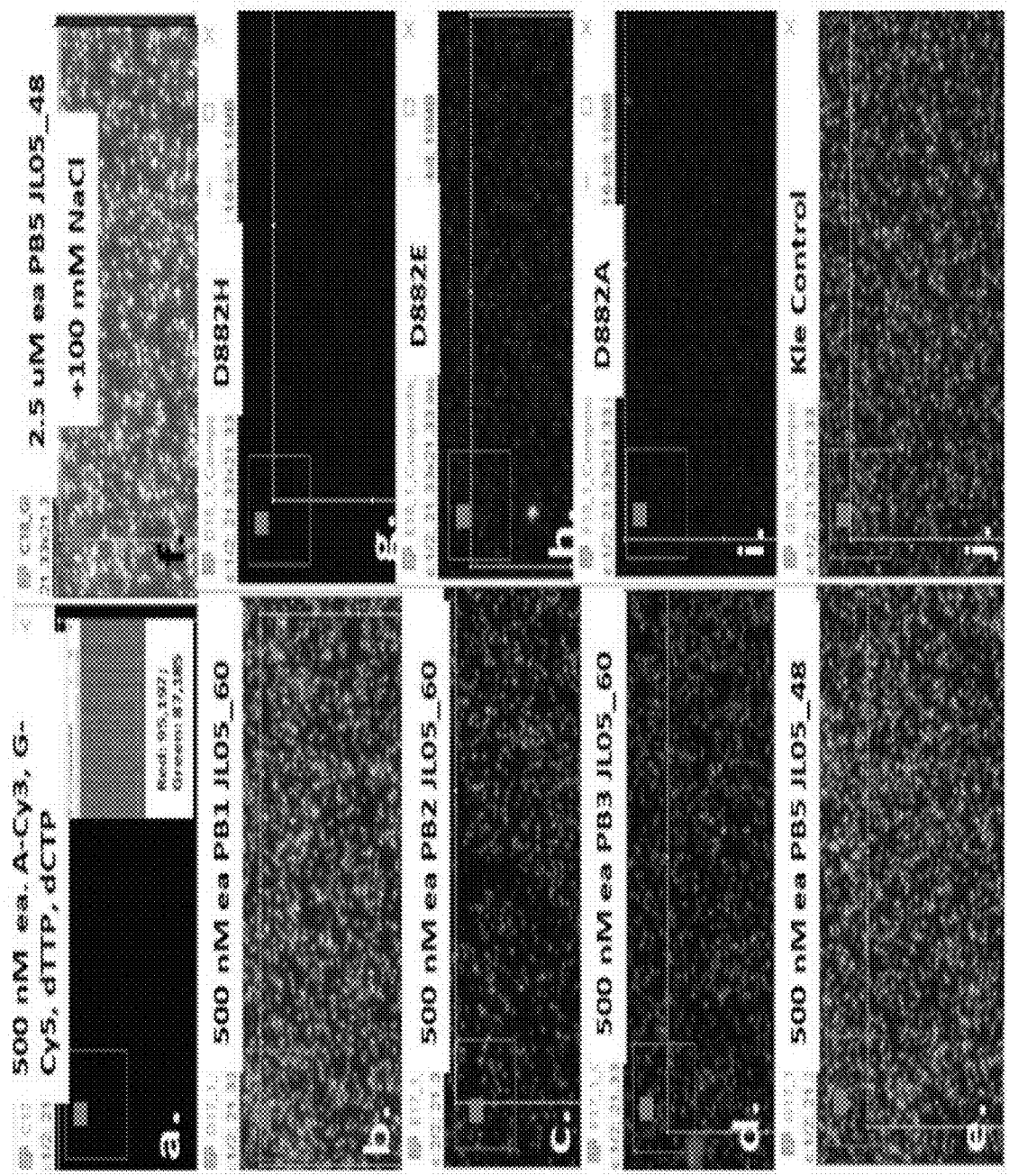
FIGS. 9A-J

- 5 Cycles:
- G: Cy3 (Green)
- A: Cy5 (Red)
- C: dark bases (both C & T)

MULTIVALENT BINDING COMPOSITION FOR NUCLEIC ACID ANALYSIS

CROSS REFERENCE

This application claims the benefit of U.S. Provisional Application No. 62/897,172 filed Sep. 6, 2019, which is incorporated herein by reference.

FIELD OF THE INVENTION

The present invention relates generally to multivalent binding compositions and their use in analyzing nucleic acid molecules. In particular, the invention relates to a multivalent binding composition having multiple copies of a nucleotide attached to a particle which effectively increases the local concentration of the nucleotide and enhances the binding signals. The multivalent binding composition can be applied, for example, in the field of sequencing and biosensor microarrays.

BACKGROUND

Nucleic acid sequencing can be used to obtain information in a wide variety of biomedical contexts, including diagnostics, prognostics, biotechnology, and forensic biology. Various sequencing methods have been developed including Maxam-Gilbert sequencing and chain-termination methods, or de novo sequencing methods including shotgun sequencing and bridge PCR, or next-generation methods including polony sequencing, 454 pyrosequencing, Illumina sequencing, SOLiD sequencing, Ion Torrent semiconductor sequencing, Heli Scope single molecule sequencing, SMRT® sequencing, and others. Despite advances in DNA sequencing, many challenges still remain unaddressed. The present disclosure provides novel solutions and approaches to addressing many of the shortcomings of existing technologies.

SUMMARY

In some embodiments the present disclosure provides method of determining the identity of a nucleotide in a target nucleic acid comprising the steps, without regard to any particular order of operations, 1) providing a composition comprising: a target nucleic acid comprising two or more repeats of an identical sequence; two or more primer nucleic acids complementary to one or more regions of said target nucleic acid; and two or more polymerase molecules; 2) contacting said composition with a multivalent binding composition comprising a polymer-nucleotide conjugate under conditions sufficient to allow a binding complex to be formed between said polymer-nucleotide conjugate and the composition of step (a), wherein the polymer-nucleotide conjugate comprises two or more copies of a nucleotide and optionally one or more detectable labels; and 3) detecting said binding complex, thereby establishing the identity of said nucleotide in the target nucleic acid polymer. In some further embodiments, the present disclosure provides said method, wherein the target nucleic acid is DNA, and/or wherein the target nucleic acid has been replicated, such as by any commonly practiced method of DNA replication or amplification, such as rolling circle amplification, bridge amplification, helicase dependent amplification, isothermal bridge amplification, rolling circle multiple displacement amplification (RCA/MDA) and/or recombinase based methods of replication or amplification. In some further embodiments, the present disclosure provides said method, wherein the detectable label is a fluorescent label and/or wherein detecting the complex comprises a fluorescence measurement. In some further embodiments, the present disclosure provides said method wherein the multivalent binding composition comprises one type of polymer-nucleotide conjugate, wherein the multivalent binding composition comprises two or more types of polymer-nucleotide conjugates, and/or wherein each type of the two or more types of polymer-nucleotide conjugates comprises a different type of nucleotide. In some embodiments, the present disclosure provides said method wherein the binding complex further comprises a blocked nucleotide, especially wherein the blocked nucleotide is a 3'-O-azidomethyl, a 3'-O-alkyl hydroxylamino or 3'-O-methyl nucleotide. In some further embodiments, the present disclosure provides said method wherein the contacting is done in the presence of strontium ions, magnesium ions, and/or calcium ions. In some embodiments, the present disclosure provides said method wherein the polymerase molecule is catalytically inactive, such as where the polymerase molecule been rendered catalytically inactive by mutation, by chemical modification, or by the absence of a necessary ion or cofactor. In some embodiments, the present disclosure also provides said method wherein the polymerase molecule is catalytically active, and/or wherein the binding complex does not comprise a blocked nucleotide. In some embodiments, the present disclosure provides said method wherein the binding complex has a persistence time of greater than 2 seconds and/or wherein the method is or may be carried out at a temperature of at or above 15° C., at or above 20° C., at or above 25° C., at or above 35° C., at or above 37° C., at or above 42° C. at or above 55° C. at or above 60° C., or at or above 72° C., or within a range defined by any of the foregoing. In some embodiments, the present disclosure provides said method wherein the binding complex is deposited on, attached to, or hybridized to, a surface showing a contrast to noise ratio in the detecting step of greater than 20. In some embodiments, the present disclosure provides said method wherein the composition is deposited under buffer conditions incorporating a polar aprotic solvent. In some embodiments, the present disclosure provides said method wherein the contacting is performed under a condition that stabilizes said binding complex when said nucleotide is complementary to a next base of said target nucleic acid, and destabilizes said binding complex when said nucleotide is not complementary to said next base of said target nucleic acid. In some embodiments, the present disclosure provides said method wherein said polymer-nucleotide conjugate comprises a polymer having a plurality of branches and said plurality of copies of said first nucleotide are attached to said branches, especially wherein said first polymer has a star, comb, cross-linked, bottle brush, or dendrimer configuration. In some embodiments, the present disclosure provides said method wherein said polymer-nucleotide conjugate comprises one or more binding groups selected from the group consisting of avidin, biotin, affinity tag, and combinations thereof. In some embodiments, the present disclosure provides said method further comprising a dissociation step that destabilizes said binding complex formed between the composition of (a) and the polymer-nucleotide conjugate to remove said polymer-nucleotide conjugate. In some embodiments, the present disclosure provides said method further comprising an extension step to incorporate into said primer nucleic acid a nucleotide that is complementary to said next base of the target nucleic acid, and optionally wherein the extension step occurs currently as or after said dissociation step.

In some embodiments, the present disclosure provides a composition comprising a branched polymer having two or more branches and two or more copies of a nucleotide, wherein said nucleotide is attached to a first plurality of said branches or arms, and optionally, wherein one or more interaction moieties are attached to a second plurality of said branches or arms. In some embodiments, said composition may further comprise one or more labels on the polymer. In some embodiments, the present disclosure provides said composition wherein the nucleoside has a surface density of at least 4 nucleotides per polymer. In some embodiments, the present disclosure provides said composition comprising or incorporating a nucleotide or nucleotide analog that is modified so as to prevent its incorporation into an extending nucleic acid chain during a polymerase reaction. In some embodiments, said composition may comprise or incorporate a nucleotide or nucleotide analog that is reversibly modified so as to prevent its incorporation into an extending nucleic acid chain during a polymerase reaction. In some embodiments, the present disclosure provides said composition wherein one or more labels comprise a fluorescent label, a FRET donor, and/or a FRET acceptor. In some embodiments, said composition may comprise 2, 3, 4, 5, 6, 7, 8, 9, 10, 11, 12, 13, 14, 15, 16 or more branches or arms, or 2, 4, 8, 16, 32, 64, or more, branches or arms. In some embodiments, the branches or arms may radiate from a central moiety. In some embodiments, said composition may comprise one or more interaction moieties, which interaction moieties may comprise avidin or streptavidin; a biotin moiety; an affinity tag; an enzyme, antibody, minibody, receptor, or other protein; a non-protein tag; a metal affinity tag, or any combination thereof. In some embodiments, the present disclosure provides said composition wherein the polymer comprises polyethylene glycol, polypropylene glycol, polyvinyl acetate, polylactic acid, or polyglycolic acid. In some embodiments, the present disclosure provides said composition wherein the nucleotide or nucleotide analog is attached to the branch or arm through a linker; and especially wherein the linker comprises PEG, and wherein the PEG moiety has an average molecular weight of about 1K, about 2K, about 3K, about 4K, about 5K, about 10K, about 15K, about 20K, about 50K, about 100K, about 150K, or about 200K, or greater than about 200K. In some embodiments, the present disclosure provides said composition wherein the linker comprises PEG, and wherein the PEG moiety has an average molecular weight of between about 5K and about 20K. In some embodiments, the present disclosure provides said composition wherein at least one nucleotide or nucleotide analog comprises a deoxyribonucleotide, a ribonucleotide, a deoxyribonucleoside, or a ribonucleoside; and/or wherein the nucleotide or nucleotide analog is conjugated to the linker through the 5' end of the nucleotide or nucleotide analog. In some embodiments, the present disclosure provides said composition wherein one of the nucleotides or nucleotide analogs comprises deoxyadenosine, deoxyguanosine, thymidine, deoxyuridine, deoxycytidine, adenosine, guanosine, 5-methyl-uridine, and/or cytidine; and wherein the length of the linker is between 1 and 1,000 nm. In some embodiments, the present disclosure provides said composition wherein at least one nucleotide or nucleotide analog is a nucleotide that has been modified to inhibit elongation during a polymerase reaction or a sequencing reaction, such as wherein the at least one nucleotide or nucleotide analog is a nucleotide that lacks a 3' hydroxyl group; a nucleotide that has been modified to contain a blocking group at the 3' position; and/or a nucleotide that has been modified with a 3'-O-azido group, a 3'-O-azidomethyl group, a 3'-O-alkyl hydroxylamino group, a 3'-phosphorothioate group, a 3'-O-malonyl group, or a 3'-O-benzyl group. In some embodiments, the present disclosure provides said composition wherein at least one nucleotide or nucleotide analog is a nucleotide that has not been modified at the 3' position.

In some embodiments, the present disclosure provides a method of determining the sequence of a nucleic acid molecule comprising the steps, without regard to any particular order, of 1) providing a nucleic acid molecule comprising a template strand and a complementary strand that is at least partially complementary to the template strand; 2) contacting the nucleic acid molecule with the one or more nucleic acid binding composition as described herein; 3) detecting binding of the nucleic acid binding composition to the nucleic acid molecule, and 4) determining an identity of a terminal nucleotide to be incorporated into said complementary strand of said nucleic acid molecule. In some embodiments, the present disclosure provides said method, further comprising incorporating said terminal nucleotide into said complementary strand, and repeating said contacting, detecting, and incorporating steps for one or more additional iterations, thereby determining the sequence of said template strand of said nucleic acid molecule. In some embodiments, the present disclosure provides said method, wherein said nucleic acid molecule is tethered to a solid support; and especially wherein the solid support comprises a glass or polymer substrate, at least one hydrophilic polymer coating layer, and a plurality of oligonucleotide molecules attached to at least one hydrophilic polymer coating layer. In some embodiments, the present disclosure provides said method, further comprising embodiments wherein at least one hydrophilic polymer coating layer comprises PEG; and/or wherein at least one hydrophilic polymer layer comprises a branched hydrophilic polymer having at least 8 branches. In some embodiments, the present disclosure provides said method, wherein the plurality of oligonucleotide molecules is present at a surface density of at least 500 molecules/mm$^2$, at least 1,000 molecules/mm$^2$, at least 5,000 molecules/mm$^2$, at least 10,000 molecules/mm$^2$, at least 20,000 molecules/mm$^2$, at least 50,000 molecules/mm$^2$, at least 100,000 molecules/mm$^2$, or at least 500,000 molecules/mm$^2$. In some embodiments, the present disclosure provides said method, wherein said nucleic acid molecule has been clonally-amplified on a solid support. In some embodiments, the present disclosure provides said method, wherein the clonal amplification comprises the use of a polymerase chain reaction (PCR), multiple displacement amplification (MDA), transcription-mediated amplification (TMA), nucleic acid sequence-based amplification (NASBA), strand displacement amplification (SDA), real-time SDA, bridge amplification, isothermal bridge amplification, rolling circle amplification, circle-to-circle amplification, helicase-dependent amplification, recombinase-dependent amplification, single-stranded binding (SSB) protein-dependent amplification, or any combination thereof. In some embodiments, the present disclosure provides said method, wherein the one or more nucleic acid binding compositions are labeled with fluorophores and the detecting step comprises use of fluorescence imaging; and especially wherein the fluorescence imaging comprises dual wavelength excitation/four wavelength emission fluorescence imaging. In some embodiments, the present disclosure provides said method, wherein four different nucleic acid binding compositions, each comprising a different nucleotide or nucleotide analog, are used to determine the identity of the terminal nucleotide, wherein the four different nucleic acid binding compositions are labeled with separate respective fluorophores, and wherein the detecting step comprises simultaneous excitation at a wavelength sufficient to excite all four fluorophores and imaging of fluorescence emission at wavelengths sufficient to detect each respective fluorophore. In some embodiments, the present disclosure provides said method, wherein four different nucleic acid binding compositions, each comprising a different nucleotide or nucleotide analog, are used to determine the identity of the terminal nucleotide, wherein the four different nucleic acid binding compositions are labeled with Cy3, Cy3.5, Cy5, and Cy5.5 respectively, and wherein the detecting step comprises simultaneous excitation at any two of 532 nm, 568 nm and 633 nm, and imaging of fluorescence emission at about 570 nm, 592 nm, 670 nm, and 702 nm respectively; and/or wherein the fluorescence imaging comprises dual wavelength excitation/dual wavelength emission fluorescence imaging. In some embodiments, the present disclosure provides said method, wherein four different nucleic acid binding compositions, each comprising a different nucleotide or nucleotide analog, are used to determine the identity of the terminal nucleotide, wherein one, two, three, or four different nucleic acid binding compositions are respectively labeled, each with a with distinct fluorophore or set of fluorophores, and wherein the detecting step comprises simultaneous excitation at a wavelength sufficient to excite one, two, three, or four fluorophores or sets of fluorophores, and imaging of fluorescence emission at wavelengths sufficient to detect each respective fluorophore. In some embodiments, the present disclosure provides said method, wherein three different nucleic acid binding compositions, each comprising a different nucleotide or nucleotide analog, are used to determine the identity of the terminal nucleotide, wherein one, two, or three different nucleic acid binding compositions are respectively labeled, each with a with distinct fluorophore or set of fluorophores, and wherein the detecting step comprises simultaneous excitation at a wavelength sufficient to excite one, two, or three, fluorophores or sets of fluorophores, and imaging of fluorescence emission at wavelengths sufficient to detect each respective fluorophore, and wherein detection of the fourth nucleotide is determined or determinable with reference to the location of "dark" or unlabeled spots or target nucleotides. In some embodiments, the present disclosure provides said method, wherein the multivalent binding composition consists of three types of polymer-nucleotide conjugates and wherein each type of the three types of polymer-nucleotide conjugates comprises a different type of nucleotide. In some embodiments, the present disclosure provides said method, wherein the detection of the binding complex is performed in the absence of unbound or solution-borne polymer nucleotide conjugates.

In some embodiments, the present disclosure provides said method, wherein four different nucleic acid binding compositions, or three different nucleic acid binding compositions, each comprising a different nucleotide or nucleotide analog, are used to determine the identity of the terminal nucleotide, wherein one of the four or three different nucleic acid binding compositions is labeled with a first fluorophore, one is labeled with a second fluorophore, one is labeled with both the first and second fluorophore, and one is not labeled or is absent, and wherein the detecting step comprises simultaneous excitation at a first excitation wavelength and a second excitation wavelength and images are acquired at a first fluorescence emission wavelength and a second fluorescence emission wavelength. In some embodiments, the present disclosure provides said method, wherein the first fluorophore is Cy3, the second fluorophore is Cy5, the first excitation wavelength is 532 nm or 568 nm, the second excitation wavelength is 633 nm, the first fluorescence emission wavelength is about 570 nm, and the second fluorescence emission wavelength is about 670 nm. In some embodiments, the present disclosure provides said method, wherein the detection label can comprise one or more portions of a FRET pair, such that multiple classifications can be performed under a single excitation and imaging step. In some embodiments, the present disclosure provides said method, wherein a sequencing reaction cycle comprising the contacting, detecting, and incorporating/extending steps is performed in less than 30 minutes in less than 20 minutes, or in less than 10 minutes. In some embodiments, the present disclosure provides said method, wherein an average Q-score for base calling accuracy over a sequencing run is greater than or equal to 30, and/or greater than or equal to 40. In some embodiments, the present disclosure provides said method, wherein at least 50%, at least 60%, at least 70%, at least 80%, or at least 90% of the terminal nucleotides identified have a Q-score of greater than 30 and/or greater than or equal to 40. In some embodiments, the present disclosure provides said method, herein at least 95% of the terminal nucleotides identified have a Q-score of greater than 30.

In some embodiments, the present disclosure provides a reagent comprising one or more nucleic acid binding compositions as disclosed herein and a buffer. For example, in some embodiments, the present disclosure provides a reagent, wherein said reagent comprises 1, 2, 3, 4, or more nucleic acid binding compositions, wherein each nucleic acid binding composition comprises a single type of nucleotide. In some embodiments, a reagent of the present disclosure comprises 1, 2, 3, 4, or more nucleic acid binding compositions, wherein each nucleic acid binding composition comprises a single type of nucleotide or nucleotide analog, and wherein said nucleotide or nucleotide analog may respectively correspond to one or more from the group consisting of ATP, ADP, AMP, dATP, dADP, and dAMP; one or more from the group consisting of TTP, TDP, TMP, dTTP, dTDP, dTMP, UTP, UDP, UMP, dUTP, dUDP, and dUMP; one or more from the group consisting of CTP, CDP, CMP, dCTP, dCDP, and dCMP; and one or more from the group consisting of GTP, GDP, GMP, dGTP, dGDP, and dGMP. In some other examples or some further examples, the present disclosure provides a reagent comprising or further comprising 1, 2, 3, 4, or more nucleic acid binding compositions, wherein each nucleic acid binding composition comprises a single type of nucleotide or nucleotide analog, and wherein said nucleotide or nucleotide analog may respectively correspond to one or more from the group consisting of ATP, ADP, AMP, dATP, dADP, dAMP, TTP, TDP, TMP, dTTP, dTDP, dTMP, UTP, UDP, UMP, dUTP, dUDP, dUMP, CTP, CDP, CMP, dCTP, dCDP, dCMP, GTP, GDP, GMP, dGTP, dGDP, and dGMP.

In some embodiments, the present disclosure provides a kit comprising the nucleic acid binding composition as disclosed herein and/or a reagent as disclosed herein, and/or one or more buffers; and instructions for the use thereof.

In some embodiments, the present disclosure provides a system for performing the method or methods disclosed herein, comprising a nucleic acid binding composition as disclosed herein, and/or a reagent a, s disclosed herein. In some embodiments, a system is configured to iteratively perform the sequential contacting of said tethered nucleic acid molecules with said nucleic acid binding composition and/or said reagent; and for the detection of binding of the nucleic acid binding compositions to the one or more nucleic acid molecules.

In some embodiments, the present disclosure provides a composition comprising a particle, said particle comprising a plurality of enzyme or protein binding substrates, wherein the enzyme or protein binding substrates bind with one or more enzymes or proteins to form one or more binding complexes, and wherein said binding may be monitored or identified by observation of the location, presence, or persistence of one or more binding complexes. In some embodiments, said particle may comprise a polymer, branched polymer, dendrimer, liposome, micelle, nanoparticle, or quantum dot. In some embodiments, said substrate may comprise a nucleotide, a nucleoside, a nucleotide analog, or a nucleoside analog. In some embodiments, the enzyme or protein binding substrate may comprise an agent that can bind with a polymerase. In some embodiments, the enzyme or protein may comprise a polymerase. In some embodiments, said observation of the location, presence, or persistence of one or more binding complexes may comprise fluorescence detection. In some embodiments, the present disclosure provides a composition comprising multiple distinct particles as disclosed herein, wherein each particle comprises a single type of nucleoside or nucleoside analog, and wherein each nucleoside or nucleoside analog is associated with a fluorescent label of a detectably different emission or excitation wavelength. In some embodiments, the present disclosure provides said composition further comprising one or more labels on the particle. In some embodiments, the present disclosure provides said composition wherein the nucleoside or nucleoside analog has a surface density of at least 4 nucleosides or nucleoside analogs. In some embodiments, the present disclosure provides said composition wherein the nucleoside or nucleoside analog has a surface density of between 0.001 and 1,000,000 per $\mu m^2$, between 0.01 and 1,000,000 per $\mu m^2$, between 0.1 and 1,000,000 per $\mu m^2$, between 1 and 1,000,000 per $\mu m^2$, between 10 and 1,000,000 per $\mu m^2$, between 100 and 1,000,000 per $\mu m^2$, between 1,000 and 1,000,000 per $\mu m^2$, between 1,000 and 100,000 per $\mu m^2$, between 10,000 and 100,000 per $\mu m^2$, or between 50,000 and 100,000 per $\mu m^2$, or within a range defined by nay two of the foregoing values. In some embodiments, the present disclosure provides said composition wherein the nucleoside or nucleoside analog is present within a nucleotide or nucleotide analog. In some embodiments, the present disclosure provides said composition wherein the composition comprises or incorporates a nucleotide or nucleotide analog that is modified so as to prevent its incorporation into an extending nucleic acid chain during a polymerase reaction. In some embodiments, the present disclosure provides said composition wherein the composition comprises or incorporates a nucleotide or nucleotide analog that is reversibly modified so as to prevent its incorporation into an extending nucleic acid chain during a polymerase reaction. In some embodiments, the present disclosure provides said composition wherein one or more labels comprise a fluorescent label, a FRET donor, and/or a FRET acceptor. In some embodiments, the present disclosure provides said composition wherein the substrate is attached to the particle through a linker. In some embodiments, the present disclosure provides said composition wherein at least one nucleotide or nucleotide analog is a nucleotide that has been modified to inhibit elongation during a polymerase reaction or a sequencing reaction, such as, for example, a nucleotide that lacks a 3' hydroxyl group; a nucleotide that has been modified to contain a blocking group at the 3' position; a nucleotide that has been modified with a 3'-O-azido group, a 3'-0-azidomethyl group, a 3'-O-alkyl hydroxylamino group, a 3'-phosphorothioate group, a 3'-O-malonyl group, or a 3'-O-benzyl group; and/or a nucleotide that has not been modified at the 3' position.

In some embodiments, the present disclosure provides a method of determining the sequence of a nucleic acid molecule comprising the steps, without regard to order, of 1) providing a nucleic acid molecule comprising a template strand and a complementary strand that is at least partially complementary to the template strand; 2) contacting the nucleic acid molecule with the one or more nucleic acid binding composition as described herein; 3) detecting binding of the nucleic acid binding composition to the nucleic acid molecule, and 4) determining an identity of a terminal nucleotide to be incorporated into said complementary strand of said nucleic acid molecule. In some embodiments, said method may further comprise incorporating said terminal nucleotide into said complementary strand, and repeating said contacting, detecting, and incorporating steps for one or more additional iterations, thereby determining the sequence of said template strand of said nucleic acid molecule. In some embodiments, the present disclosure provides said method wherein said nucleic acid molecule has been clonally-amplified on a solid support. In some embodiments, the present disclosure provides said method wherein the clonal amplification comprises the use of a polymerase chain reaction (PCR), multiple displacement amplification (MDA), transcription-mediated amplification (TMA), nucleic acid sequence-based amplification (NASBA), strand displacement amplification (SDA), real-time SDA, bridge amplification, isothermal bridge amplification, rolling circle amplification, circle-to-circle amplification, helicase-dependent amplification, recombinase-dependent amplification, single-stranded binding (SSB) protein-dependent amplification, or any combination thereof. In some embodiments, the present disclosure provides said method wherein a sequencing reaction cycle comprising the contacting, detecting, and incorporating steps is performed in less than 30 minutes, less than 20 minutes, or in less than 10 minutes. In some embodiments, the present disclosure provides said method wherein an average Q-score for base calling accuracy over a sequencing run is greater than or equal to 30, or greater than or equal to 40. In some embodiments, the present disclosure provides said method wherein at least 50%, at least 60%, at least 70%, at least 80%, or at least 90% of the terminal nucleotides identified have a Q-score of greater than 30; or greater than 40. In some embodiments, the present disclosure provides said method wherein at least 95% of the terminal nucleotides identified have a Q-score of greater than 30.

In some embodiments, the present disclosure provides a reagent comprising one or more nucleic acid binding compositions as disclosed herein, and a buffer. In some embodiments, the present disclosure provides said reagent, wherein said reagent comprises 1, 2, 3, 4, or more nucleic acid binding compositions, wherein each nucleic acid binding composition comprises a single type of nucleotide or nucleotide analog, and wherein said nucleotide or nucleotide analog comprises a nucleotide, nucleotide analog, nucleoside, or nucleoside analog. In some embodiments, the present disclosure provides said method wherein said reagent comprises 1, 2, 3, 4, or more nucleic acid binding compositions, wherein each nucleic acid binding composition comprises a single type of nucleotide or nucleotide analog, and wherein said nucleotide or nucleotide analog may respectively correspond to one or more from the group consisting of ATP, ADP, AMP, dATP, dADP, and dAMP; one or more from the group consisting of TTP, TDP, TMP, dTTP, dTDP, dTMP, UTP, UDP, UMP, dUTP, dUDP, and dUMP; one or more from the group consisting of CTP, CDP, CMP, dCTP, dCDP, and dCMP; and one or more from the group consisting of GTP, GDP, GMP, dGTP, dGDP, and dGMP. In some embodiments, the present disclosure provides said method wherein said reagent comprises 1, 2, 3, 4, or more nucleic acid binding compositions, wherein each nucleic acid binding composition comprises a single type of nucleotide or nucleotide analog, and wherein said nucleotide or nucleotide analog may respectively correspond to one or more from the group consisting of ATP, ADP, AMP, dATP, dADP, dAMP TTP, TDP, TMP, dTTP, dTDP, dTMP, UTP, UDP, UMP, dUTP, dUDP, dUMP, CTP, CDP, CMP, dCTP, dCDP, dCMP, GTP, GDP, GMP, dGTP, dGDP, and dGMP.

In some embodiments, the present disclosure provides a kit comprising any of the compositions disclosed herein; and/or any of the reagents disclosed herein; one or more buffers; and instructions for the use thereof.

In some embodiments, the present disclosure provides a system for performing any of the methods disclosed herein; wherein said methods may comprise use of any of the compositions as disclosed herein; and/or any of the reagents as disclosed herein; one or more buffers, and one or more nucleic acid molecules optionally tethered or attached to a solid support, wherein said system is configured to iteratively perform for the sequential contacting of said nucleic acid molecules with said composition and/or said reagent; and for the detection of binding of the nucleic acid binding compositions to the one or more nucleic acid molecules.

In some embodiments, the present disclosure provides a composition as disclosed herein for use in increasing the contrast to noise ratio (CNR) of a labeled nucleic acid complex bound to or associated with a surface.

In some embodiments, the present disclosure provides a composition as disclosed herein for use in establishing or maintaining control over the persistence time of a signal from a labeled nucleic acid complex bound to or associated with a surface.

In some embodiments, the present disclosure provides a composition as disclosed herein for use in establishing or maintaining control over the persistence time of a fluorescence, luminescence, electrical, electrochemical, colorimetric, radioactive, magnetic, or electromagnetic signal from a labeled nucleic acid complex bound to or associated with a surface.

In some embodiments, the present disclosure provides a composition as disclosed herein for use in increasing the specificity, accuracy, or read length of a nucleic acid sequencing and/or genotyping application.

In some embodiments, the present disclosure provides a composition as disclosed herein for use in increasing the specificity, accuracy, or read length in a sequencing by binding, sequencing by synthesis, single molecule sequencing, or ensemble sequencing method.

In some embodiments, the present disclosure provides a reagent as disclosed herein for use in increasing the contrast to noise ratio (CNR) of a labeled nucleic acid complex bound to or associated with a surface.

In some embodiments, the present disclosure provides a reagent as disclosed herein for use in establishing or maintaining control over the persistence time of a signal from a labeled nucleic acid complex bound to or associated with a surface.

In some embodiments, the present disclosure provides a reagent as disclosed herein for use in establishing or maintaining control over the persistence time of a fluorescence, luminescence, electrical, electrochemical, colorimetric, radioactive, magnetic, or electromagnetic signal from a labeled nucleic acid complex bound to or associated with a surface.

In some embodiments, the present disclosure provides a reagent as disclosed herein for use in increasing the specificity, accuracy, or read length of a nucleic acid sequencing and/or genotyping application.

In some embodiments, the present disclosure provides a reagent as disclosed herein for use in increasing the specificity, accuracy, or read length in a sequencing by binding, sequencing by synthesis, single molecule sequencing, or ensemble sequencing method.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in its entirety. In the event of a conflict between a term herein and a term in an incorporated reference, the term herein controls.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A-H illustrate the steps utilizing a non-limiting examples of multivalent binding composition for sequencing a target nucleic acid: FIG. 1A illustrates a non-limiting example 4—of attaching target nucleic acid to a surface; FIG. 1B illustrates clonally the target nucleic acid to form clusters of amplified target nucleic acid molecules; FIG. 1C illustrates a non-limiting example of priming the target nucleic acid to produce a primed target nucleic acid; FIG. 1D illustrates a non-limiting example of contacting the primed target nucleic acid to the multivalent binding composition and polymerase to form a binding complex; FIG. 1E illustrates a non-limiting example of the images of the binding complex captured on the surface; FIG. 1F illustrates a non-limiting example of extending the primer strand by one nucleotide; FIG. 1G illustrates a non-limiting example of another cycle of contacting the primed target nucleic acid to the multivalent binding composition and polymerase to form a binding complex; and FIG. 1I illustrates non-limiting examples of the images of binding complex captured on the surface in subsequent sequencing cycles.

FIG. 2A-2B illustrate a non-limiting example of detecting target nucleic acid using the polymer-nucleotide conjugates. FIG. 2A shows the step of contacting the polymerase and polymer-nucleotide conjugates to some nucleic acid molecules; FIG. 2B shows the binding complex formed between the polymerase, polymer-nucleotide conjugates, and the target nucleic acid molecules.

FIG. 5A shows polymer-nucleotide conjugates having various multi-arm configurations; FIG. 5B shows a polymer-nucleotide conjugate having the polymer branch radiating from the center; and FIG. 5C shows polymer-nucleotide conjugates having the binding moiety biotin.

FIGS. 7A-7G show fluorescence images of multivalent polyethylene glycol (PEG) polymer-nucleotide (base-labeled) conjugates, having an effective nucleotide concentration of 500 nM and varying PEG branch length, after contacting to a support surface comprising DNA templates (comprising G or A as the first base; prepared using rolling circle amplification (RCA)) in an exposure buffer comprising 20 nM Klenow polymerase and 2.5 mM Sr'. Images were acquired after washing with an imaging buffer having the same composition as the exposure buffer but lacking nucleotides and polymerase. Panels show images obtained using multivalent PEG-nucleotide ligands with arm lengths as follows. FIG. 7A: 1K PEG. FIG. 7B: 2K PEG. FIG. 7C: 3K PEG. FIG. 7D: 5K PEG. FIG. 7E: 10K PEG. FIG. 7F: 20K PEG. FIG. 7G shows images obtained using 10K PEG and an inactive klenow polymerase comprising the mutation D882H. FIG. 7H shows images obtained using 10K PEG and an inactive klenow polymerase comprising the mutation D882E. FIG. 7I shows images obtained using 10K PEG and an inactive klenow polymerase comprising the mutation D882A. FIG. 7G shows images obtained using 10K PEG and an active wild type klenow polymerase.

FIGS. 9A-9J show fluorescence images of the steps in a sequencing reaction using multivalent PEG-substrate compositions. FIG. 9A. Red and green fluorescent images post exposure of DNA RCA templates (G and A first base) to 500 nM base labeled nucleotides (A-Cy3 and G-Cy5) in exposure buffer containing 20 nM Klenow polymerase and 2.5 mM $Sr^{+2}$. Images were collected after washing with imaging buffer with the same composition as the exposure buffer but containing no nucleotides or polymerase. Contrast was scaled to maximize visualization of the dimmest signals, but no signals persisted following washing with imaging buffer (a. inset). FIGS. 9B-9E: fluorescence images showing multivalent PEG-nucleotide (base-labeled) ligands PB1 (FIG. 9B), PB2 (FIG. 9C), PB3 (FIG. 9D), and PB5 (FIG. 9E) having an effective nucleotide concentration of 500 nM after mixing in the exposure buffer and imaging in the imaging buffer as described above. FIG. 9F: fluorescence image showing multivalent PEG-nucleotide (base-labeled) ligand PB5 at 2.5 uM after mixing in the exposure buffer and imaging in the imaging buffer as above. FIGS. 9G-9I. Fluorescence images showing further base discrimination by exposure of the multivalent binding composition to inactive mutants of klenow polymerase (FIG. 9G. D882H; FIG. 9H. D882E; FIG. 9I. D882A) vs. the wild type Klenow (control) enzyme (FIG. 9J).

FIG. 10A shows images and expected sequences for templates taken after each sequencing cycle; and FIG. 10B shows aligned sequencing results utilizing the images taken in FIG. 10A.

DETAILED DESCRIPTION

I. Definitions

Figure 1D:
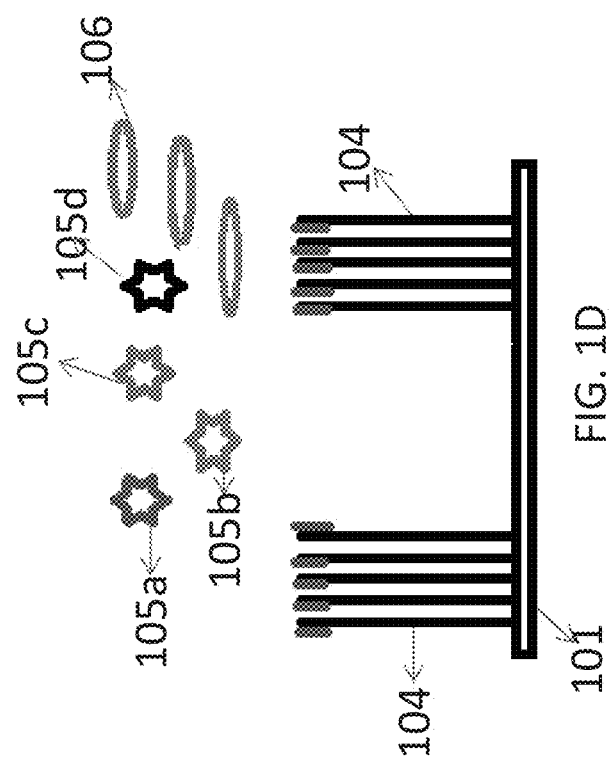

As used herein, "nucleic acid" (also referred to as a "polynucleotide", "oligonucleotide", ribonucleic acid (RNA), or deoxyribonucleic acid (DNA)) is a linear polymer of two or more nucleotides joined by covalent internucleosidic linkages, or variants or functional fragments thereof. In naturally occurring examples of nucleic acids, the internucleoside linkage is typically a phosphodiester bond. However, other examples optionally comprise other internucleoside linkages, such as phosphorothiolate linkages and may or may not comprise a phosphate group. Nucleic acids include double- and single-stranded DNA, as well as double- and single-stranded RNA, DNA/RNA hybrids, peptide-nucleic acids (PNAs), hybrids between PNAs and DNA or RNA, and may also include other types of nucleic acid modifications.

As used herein, a "nucleotide" refers to a nucleotide, nucleoside, or analog thereof. The nucleotide refers to both naturally occurring and chemically modified nucleotides and can include but are not limited to a nucleoside, a ribonucleotide, a deoxyribonucleotide, a protein-nucleic acid residue, or derivatives. Examples of the nucleotide includes an adenine, a thymine, a uracil, a cytosine, a guanine, or residue thereof; a deoxyadenine, a deoxythymine, a deoxyuracil, a deoxycytosine, a deoxyguanine, or residue thereof; a adenine PNA, a thymine PNA, a uracil PNA, a cytosine PNA, a guanine PNA, or residue or equivalents thereof, an N- or C-glycoside of a purine or pyrimidine base (e.g., a deoxyribonucleoside containing 2-deoxy-D-ribose or ribonucleoside containing D-ribose).

"Complementary," as used herein, refers to the topological compatibility or matching together of interacting surfaces of a ligand molecule and its receptor. Thus, the receptor and its ligand can be described as complementary, and furthermore, the contact surface characteristics are complementary to each other.

"Branched polymer", as used herein, refers to a polymer having a plurality of functional groups that help conjugate a biologically active molecule such as a nucleotide, and the functional group can be either on the side chain of the polymer or directly attaches to a central core or central backbone of the polymer. The branched polymer can have linear backbone with one or more functional groups coming off the backbone for conjugation. The branched polymer can also be a polymer having one or more sidechains, wherein the side chain has a site suitable for conjugation. Examples of the functional group include but are limited to hydroxyl, ester, amine, carbonate, acetal, aldehyde, aldehyde hydrate, alkenyl, acrylate, methacrylate, acrylamide, active sulfone, hydrazide, thiol, alkanoic acid, acid halide, isocyanate, isothiocyanate, maleimide, vinylsulfone, dithiopyridine, vinylpyridine, iodoacetamide, epoxide, glyoxal, dione, mesylate, tosylate, and tresylate.

"Polymerase," as used herein, refers to an enzyme that contains a nucleotide binding moiety and helps formation of a binding complex between a target nucleic acid and a complementary nucleotide. The polymerase can have one or more activities including, but not limited to, base analog detection activities, DNA polymerization activity, reverse transcriptase activity, DNA binding, strand displacement activity, and nucleotide binding and recognition. The polymerase can include catalytically inactive polymerase, catalytically active polymerase, reverse transcriptase, and other enzymes containing a nucleotide binding moiety.

"Persistence time," as used herein, refers to the length of time that a binding complex, which is formed between the target nucleic acid, a polymerase, a conjugated or unconjugated nucleotide, remains stable without any binding component dissociates from the binding complex. The persistence time is indicative of the stability of the binding complex and strength of the binding interactions. Persistence time can be measured by observing the onset and/or duration of a binding complex, such as by observing a signal from a labeled component of the binding complex. For example, a labeled nucleotide or a labeled reagent comprising one or more nucleotides may be present in a binding complex, thus allowing the signal from the label to be detected during the persistence time of the binding complex. One exemplary label is a fluorescent label.

II. Method of Analyzing Target Nucleic Acid

Disclosed herein are multivalent binding compositions and their use in analyzing nucleic acid including sequencing or other bioassay applications. An increase in binding of a nucleotide to an enzyme (e.g., polymerase) or an enzyme complex can be effected by increasing the effective concentration of the nucleotide. The increase can be achieved by increasing the concentration of the nucleotide in free solution, or by increasing the amount of the nucleotide in proximity to the relevant binding site. The increase can also be achieved by physically restricting a number of nucleotides into a limited volume thus resulting in a local increase in concentration, and such as structure may thus bind to the binding site with a higher apparent avidity than would be observed with unconjugated, untethered, or otherwise unrestricted individual nucleotide. One exemplary means of effecting such restriction is by providing a multivalent binding composition in which multiple nucleotides are bound to a particle such as a polymer, a branched polymer, a dendrimer, a micelle, a liposome, a microparticle, a nanoparticle, a quantum dot, or other suitable particle known in the art.

The multivalent binding composition disclosed herein can include at least one particle-nucleotide conjugate, and the particle-nucleotide conjugate has a plurality of copies of the same nucleotide attached to the particle. When the nucleotide is complementary to the target nucleic acid, the particle-nucleotide conjugate forms a binding complex with the polymerase and the target nucleic acid, and the binding complex exhibits increased stability and longer persistence time than the binding complex formed using a single unconjugated or untethered nucleotide.

The multivalent binding composition can be used to localize detectable signals to active regions of biochemical interactions, such as sites of protein-nucleic acid interactions, nucleic acid hybridization reactions, or enzymatic reactions, such as polymerase reactions. For instance, the multivalent binding composition described herein can be utilized to identify sites of base incorporation in elongating nucleic acid chains during polymerase reactions and to provide base discrimination for sequencing and array based applications. The increased binding between the target nucleic acid and the nucleotide in the multivalent binding composition, when the nucleotide is complementary to the target nucleic acid, provides enhanced signal that greatly improve base call accuracy and shorten imaging time.

In addition, the use of multivalent binding composition allows sequencing signals from a given sequence to originate within cluster regions containing multiple copies of the target sequence. Sequencing methods incorporating multiple copies of a target sequence have the advantage that signals can be amplified due to the presence of multiple simultaneous sequencing reactions within the defined region, each providing its own signal. The presence of multiple signals within a defined area also reduces the impact of any single skipped cycle, due to the fact that the signal from a large number of correct base calls can overwhelm the signal from a smaller number of skipped or incorrect base calls, therefore providing methods for reducing phasing errors and/or to improve read length in sequencing reactions.

The multivalent binding compositions and their use disclosed herein lead to one or more of: (i) stronger signal for better base-calling accuracy compared to conventional nucleic acid amplification and sequencing methodologies; ii) allow greater discrimination of sequence-specific signal from background signals; (iii) reduced requirements for the amount of starting material necessary, (iv) increased sequencing rate and shortened sequencing time; (v) reducing phasing errors, and (vi) improving read length in sequencing reactions.

In some embodiments, the target nucleic acid can refer to a target nucleic acid sample having one or more nucleic acid molecules. In some embodiments, the target nucleic acid can include a plurality of nucleic acid molecules. In some embodiments, the target nucleic acid can include two or more nucleic acid molecules. In some embodiments, the target nucleic acid can include two or more nucleic acid molecules having the same sequences.

A. Sequencing Target Nucleic Acid

FIG. 1A-1H illustrate one exemplified method in which the multivalent binding composition is used for sequencing a target nuclei acid. As shown in FIG. 1A, the target nucleic acid 102 can be tethered to a solid support surface 101. The target nucleic acid can be attached to the surface either directly or indirectly. Although not shown in FIG. 1A, the target nucleic acid 102 can be hybridized to an adapter, which is attached to the surface through a covalent or noncovalent bond. When one or more adapters are used to attach the target nucleic acid to the surface, the target surface can comprise a fragment that is complementary to the adapter and thus hybridize to the adaptor. In some instances, one adapter sequence may be tethered to the surface. In some instances, a plurality of adapter sequences may be tethered to the surface. In some instances, the target nucleic acid 102 can also be attached directly to the solid-support surface without the use of an adapter. The solid support can be a low non-specific binding surface.

In FIG. 1B, after the initial step of attaching the target nucleic acid to the surface of a solid support surface (e.g., through hybridization to adapters), the target nucleic acid is then clonally-amplified to form clusters of amplified nucleic acids. When the target nucleic acid is attached to the surface through an adapter, the surface density of clonally-amplified nucleic acid sequences hybridized to adapter on the support surface may span the same range as the surface density of tethered primers. The clonal amplification may be performed using a polymerase chain reaction (PCR), multiple displacement amplification (MDA), transcription-mediated amplification (TMA), nucleic acid sequence-based amplification (NASBA), strand displacement amplification (SDA), real-time SDA, bridge amplification, isothermal bridge amplification, rolling circle amplification, circle-to-circle amplification, helicase-dependent amplification, recombinase-dependent amplification, single-stranded binding (SSB) protein-dependent amplification, or any combination thereof.

FIG. 1C illustrates a non-limiting step of annealing a primer 103 to the target nucleic acid 102 to form a primed target nucleic acid 104. FIG. 1B only shows one primer being used in the annealing step, but more than one primers can be used depending on the types of target nucleic acid. In some instances, the adapter that is used to attach the target nucleic acid to the surface has the same sequence as the primer used to prepare the primed target nucleic acid. The primer may comprise forward amplification primers, reverse amplification primers, sequencing primers, and/or molecular barcoding sequences, or any combination thereof. In some instances, one primer sequence may be used in the hybridization step. In some instances, a plurality of different primer sequences may be used in the hybridization step.

As shown in FIG. 1D, the primed target nucleic acid 104 is combined with a multivalent binding composition and a polymerase 106 to form a binding complex. The non-limiting example of multivalent binding composition in FIG. 1D comprises four particle-nucleotide conjugates 105a, 105b, 105c, and 105d. Each particle-nucleotide conjugate has multiple copies of a nucleotide attached to the particle, and the four particle-nucleotide conjugates cover four types of nucleotide respectively. The particle-nucleotide conjugate having a nucleotide that is complementary to the next base on the target nucleic acid will form a binding complex with the polymerase and the target nucleic acid. In some instances, the multivalent binding composition may include one, two or three particle-nucleotide conjugates. In some embodiments, each different type of particle-nucleotide conjugate can be labeled with a separate label. In some embodiments, three of four types of nucleotide conjugates can be labeled, with a fourth either unlabeled or conjugated to an undetectable label. In some embodiments, 1, 2, 3, or 4 particle-nucleotide conjugates can be labeled, either with the same label, or each with a label corresponding to the identity of its conjugated nucleotide, with, respectively, 3, 2, 1, or no particle-nucleotide conjugates that may be either left unlabeled or conjugated to an undetectable label. In some embodiments, detection of a polymerase complex incorporating a particle-nucleotide conjugate may be carried out using four-color detection, such that conjugates corresponding to all four nucleotides are present in a sample, each conjugate having a separate label corresponding to the nucleotide conjugated thereto. In some embodiments, the four particle-nucleotide conjugates may be exposed to or contacted with the target nucleic acid at the same time; in some other embodiments, the four particle-nucleotide conjugates may be exposed to or contacted with the target nucleic acid sequentially, either individually, or in groups of two or three. In some embodiments, detection of a polymerase complex incorporating a particle-nucleotide conjugate may be carried out using three-color detection, such that conjugates corresponding to three of the four nucleotides are present in a sample, with three conjugates having a separate label corresponding to the nucleotide conjugated thereto and one conjugate having no label or being conjugated to an undetectable label. In some embodiments, only three types of conjugates are provided, such that conjugates corresponding to three of the four nucleotides are present in a sample, with three conjugates having a separate label corresponding to the nucleotide conjugated thereto and one conjugate being absent. In some embodiments, the identity of nucleotides corresponding to an unlabeled or absent nucleotide conjugate can be determined with respect to the location and/or identity of "dark" spots or locations of known target nucleic acids showing no fluorescence signal. In some embodiments, the present disclosure provides said method, wherein the detection of the binding complex is performed in the absence of unbound or solution-borne polymer nucleotide conjugates.

In some embodiments where three of the four particle-nucleotide conjugates are labeled, or where only three of the four particle-nucleotide conjugates are present, the identity of the nucleotide corresponding to the unlabeled or absent conjugate may be established by the absence of a signal or by monitoring of the presence of unlabeled complexes such as by the identification of "dark" spots or unlabeled regions in a sequencing reaction. In some embodiments, detection of a polymerase complex incorporating a particle-nucleotide conjugate may be carried out using two-color detection, such that conjugates corresponding to two of the four nucleotides are present in a sample, with two conjugates having a separate label corresponding to the nucleotide conjugated thereto and two conjugates having no label or being conjugated to an undetectable label. In some embodiments, only two of the four particle-nucleotide conjugates are labeled. In some embodiments where two of the four particle-nucleotide conjugates are labeled, the identity of the nucleotide corresponding to the unlabeled conjugate or conjugates may be established by the absence of a signal or by monitoring of the presence of unlabeled complexes such as by the identification of "dark" spots or unlabeled regions in a sequencing reaction. In some embodiments where two of the four particle-nucleotide conjugates are labeled, the four particle-nucleotide conjugates may be exposed to or contacted with the target nucleic acid sequentially, either individually, or in groups of two or three. In some embodiments two of the four particle-nucleotide conjugates may share a common label, and the four particle-nucleotide conjugates may be exposed to or contacted with the target nucleic acid sequentially, either individually, or in groups of two or three, wherein each contacting step shows the distinction between two or more different bases, such that after two, three, four, or more such contacting steps the identities of all unknown bases have been determined.

Figure 1E:
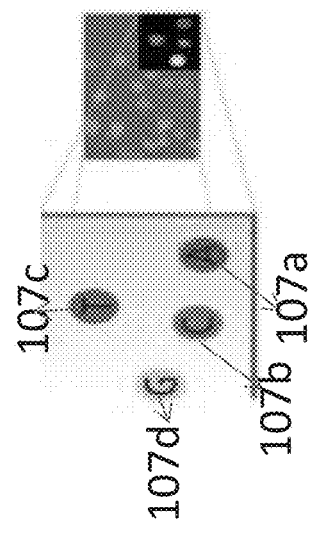

FIG. 1E shows the images captured on the surface after the binding complex is formed between the polymerase, the target nucleic acid, and the particle-nucleotide conjugate having a nucleotide commentary to the next base of the target nucleic acid. The captured image includes four binding complexes 107a, 107b, 107c, and 107d formed on the surface, and each binding complex has a different nucleotide which can be distinguished based on the label (e.g., color) on the particle-nucleotide conjugate. Because of use of the particle-nucleotide conjugate allows binding signals from a given sequence to originate within cluster regions containing multiple copies of the target sequence, the sequencing signals is greatly enhanced. Although FIG. 1E involves four particle-nucleotide conjugate, each having a different type of nucleotide, some methods can use one, two, or three particle-nucleotide conjugates, each having a different type of nucleotide and label. In some embodiments, each different type of particle-nucleotide conjugate can be labeled either with the same label, or each with a label corresponding to the identity of its conjugated nucleotide. In some embodiments, three of four types of nucleotide conjugates can be labeled, with a fourth either unlabeled or conjugated to an undetectable label. In some embodiments, 1, 2, 3, or 4 particle-nucleotide conjugates can be labeled with a separate label, with, respectively, 3, 2, 1, or no particle-nucleotide conjugates either unlabeled or conjugated to an undetectable label In some embodiments, a detection step can comprise simultaneous and/or serial excitation of up to 4 different excitation wavelengths, such as wherein the fluorescence imaging is carried out by detecting single and/or multiple fluorescence emission bands that uniquely classify each of the possible base pairing (A, G, C, or T). In some embodiments, four different nucleic acid binding compositions, each comprising a different nucleotide or nucleotide analog, may be used to determine the identity of the terminal nucleotide, wherein one of the four different nucleic acid binding compositions is labeled with a first fluorophore, one is labeled with a second fluorophore, one is labeled with both the first and second fluorophore, and one is not labeled, and wherein the detecting step comprises simultaneous excitation at a first excitation wavelength and a second excitation wavelength and images are acquired at a first fluorescence emission wavelength and a second fluorescence emission wavelength.

When the multivalent binding composition is used in replacement of single unconjugated or untethered nucleotide to form a binding complex with the polymerase and the target nucleic acid, the local concentration of the nucleotide is increased many fold, which in turn enhances the signal intensity. The formed binding complex also has a longer persistence time which in turn helps shorten the imaging step. The high signal intensity resulted from the use of the polymer nucleotide conjugate remain for the entire binding and imaging step. The strong binding between the polymerase, the primed target strand, and the nucleotide or nucleotide analog also means that the formed binding complex will remain stable during the washing step and the signal will remain at a high intensity when other reaction mixture and unmatched nucleotide analogs are washed away. After the imaging step, the binding complex can be destabilized and the primed target nucleic acid can then be extended for one base.

Figure 1F:
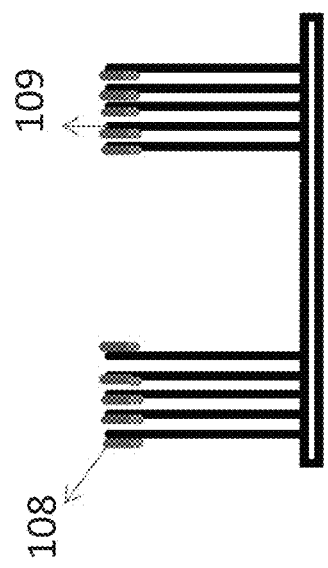
Figure 1G:
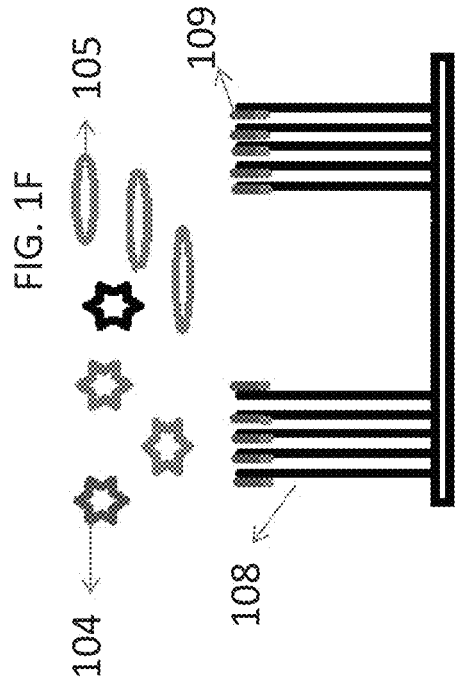

The sequencing method may further comprise incorporating the N+1 or terminal nucleotide into the primed strand as shown in FIG. 1F. In FIG. 1F, the primer strand of the primed target nucleic acid 104 can be extended for one base to form an extended nucleic acid 108. The extension step can occur after or concurrently with the destabilization of the binding complex. The primed target nucleic acid 104 can be extended using a complementary nucleotide that is attached to the particle in the particle-nucleotide conjugate, or using an unconjugated or untethered free nucleotide that is provided after the multivalent binding composition has been removed.

Figure 1H:
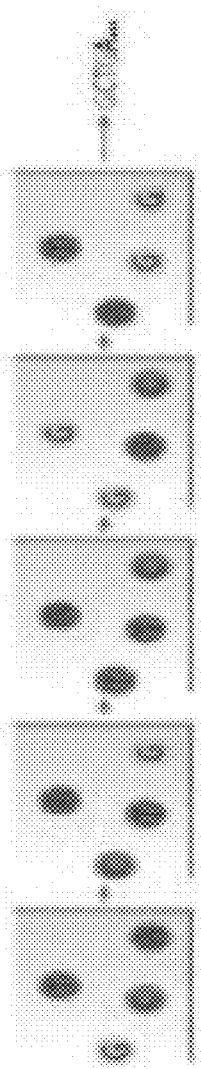

After the extension step, the contacting step as shown in FIG. 1G can be performed again to form binding complexes and imitate the next sequencing cycle. The contacting, detecting, and extension steps can be repeated for one or more cycles, thereby determining the sequence of the target nucleic acid molecule. For example, FIG. 1H shows the surface images after multiple sequencing cycles, and the images can then be processed to determine the sequences of the target nucleic acid molecules.

The extension of the primed target nucleic acid may be prevented or inhibited due to a blocked nucleotide on the strand or the use of polymerase that is catalytically inactive. When the nucleotide in the polymer-nucleotide conjugate has a blocking group that prevents the extension of the nucleic acid, incorporation of a nucleotide may be achieved by the removal of a blocking group from said nucleotide (such as by detachment of said nucleotide from its polymer, branched polymer, dendrimer, particle, or the like). When the extension of the primed target nucleic acid is inhibited due to the use of polymerase that is catalytically inactive, incorporation of a nucleotide may be achieved by the provision of a cofactor or activator such as a metal ion.

Also disclosed herein are systems configured for performing any of the disclosed nucleic acid sequencing or nucleic acid analysis methods. The system may comprise a fluid flow controller and/or fluid dispensing system configured to sequentially and iteratively contact the primed target nucleic acid molecules attached to a solid support with the disclosed polymerase and multivalent binding compositions and/or reagents. The contacting may be performed within one or more flow cells. In some instances, said flow cells may be fixed components of the system. In some instances, said flow cells may be removable and/or disposable components of the system.

The sequencing system may include an imaging module, i.e., one or more light sources, one or more optical components, and one or more image sensors for imaging and detection of binding of the disclosed nucleic acid binding compositions to target nucleic acid molecules tethered to a solid support or the interior of a flow cell. The disclosed compositions, reagents, and methods may be used for any of a variety of nucleic acid sequencing and analysis applications. Examples include, but are not limited to, DNA sequencing, RNA sequencing, whole genome sequencing, targeted sequencing, exome sequencing, genotyping, and the like.

The sequencing system may also include computer control systems that are programmed to implement methods of the disclosure. The computer system is programmed or otherwise configured to implement methods of the disclosure including nucleic acid sequencing methods, interpretation of nucleic acid sequencing data and analysis of cellular nucleic acids, such as RNA (e.g., mRNA), and characterization of cells from sequencing data. The computer system can be an electronic device of a user or a computer system that is remotely located with respect to the electronic device. The electronic device can be a mobile electronic device.

Figure 3:
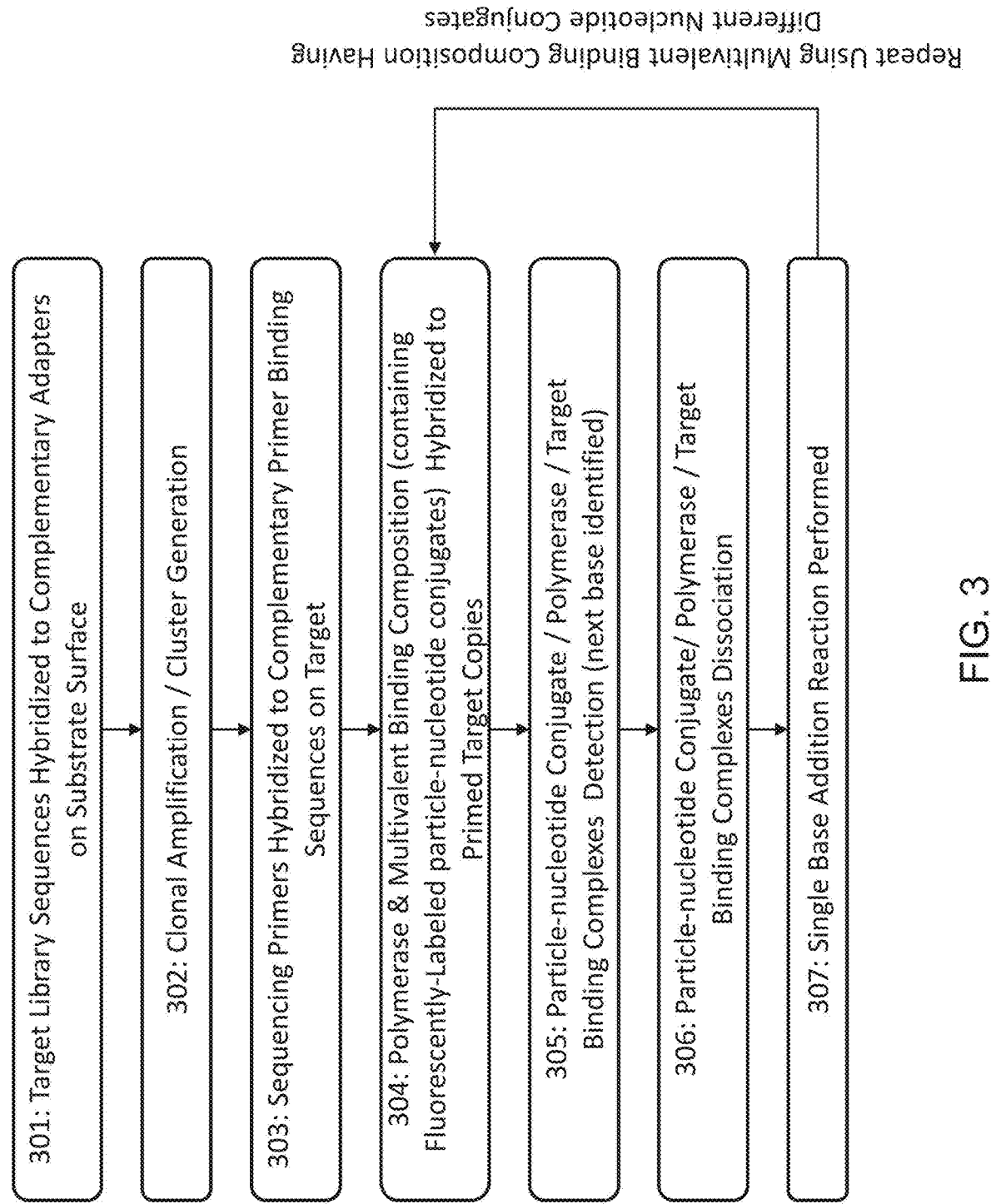
FIG. 3 shows a flow chart outlining the steps for sequencing a target nucleic acid and extending the primer strand through a single base addition.

FIG. 3 is a flowchart outlining the steps in sequencing a target nucleic acid. 301 describes a step of attaching target library sequences to a solid support surface by hybridizing the target nucleic acid molecules to complementary adapters on substrate surface. The target nucleic acid molecules can be single stranded or partially double stranded. Prior to 301, the nucleic acid molecules in the target library may have been prepared to contain fragments complementary to the adaptor sequences through ligation or other methods. 302 describes the step of clonal amplification to generate clusters of target nucleic acid molecules on the surface. 303 describes hybridizing sequencing primers to complementary primer binding sequences on the target nucleic acid to form the primed target nucleic acid. 304 describes combining the polymerase, the multivalent binding composition, which contains labeled (e.g., fluorescently-labeled) particle-nucleotide conjugates, and the primed target nucleic acid. 304 may also include a step of washing or removing the unbound reagents including polymerase and particle-nucleotide conjugate.

In 305, when the nucleotide on the particle-nucleotide conjugate is complementary to the next base of the primed target nucleic acid, the particle-nucleotide conjugate, polymerase, and primed target nucleic acid form a ternary binding complex, which can be detected by detection methods (e.g., florescence imaging) compatible with the label on the particle-nucleotide conjugate. 305 can also include measuring the persistence time of the ternary binding complex. In 306, the binding complex is destabilized to remove the binding of the particle-nucleotide conjugate and polymerase. The dissociation can be achieved by placing the binding complex in a condition (e.g., adding Strontium ions) that will change the conformation of the polymerase and destabilize the binding. 306 may also include a step of washing or removing the dissociated particle-nucleotide conjugate and/or polymerase. 307 describes the step of extending the primed strand of the primed target nucleic acid by a single base addition reaction. After the single base extension, steps 304, 305, 306, and 307 can be repeated in multiple cycles to determine the sequences of the target nucleic acid.

Figure 4:
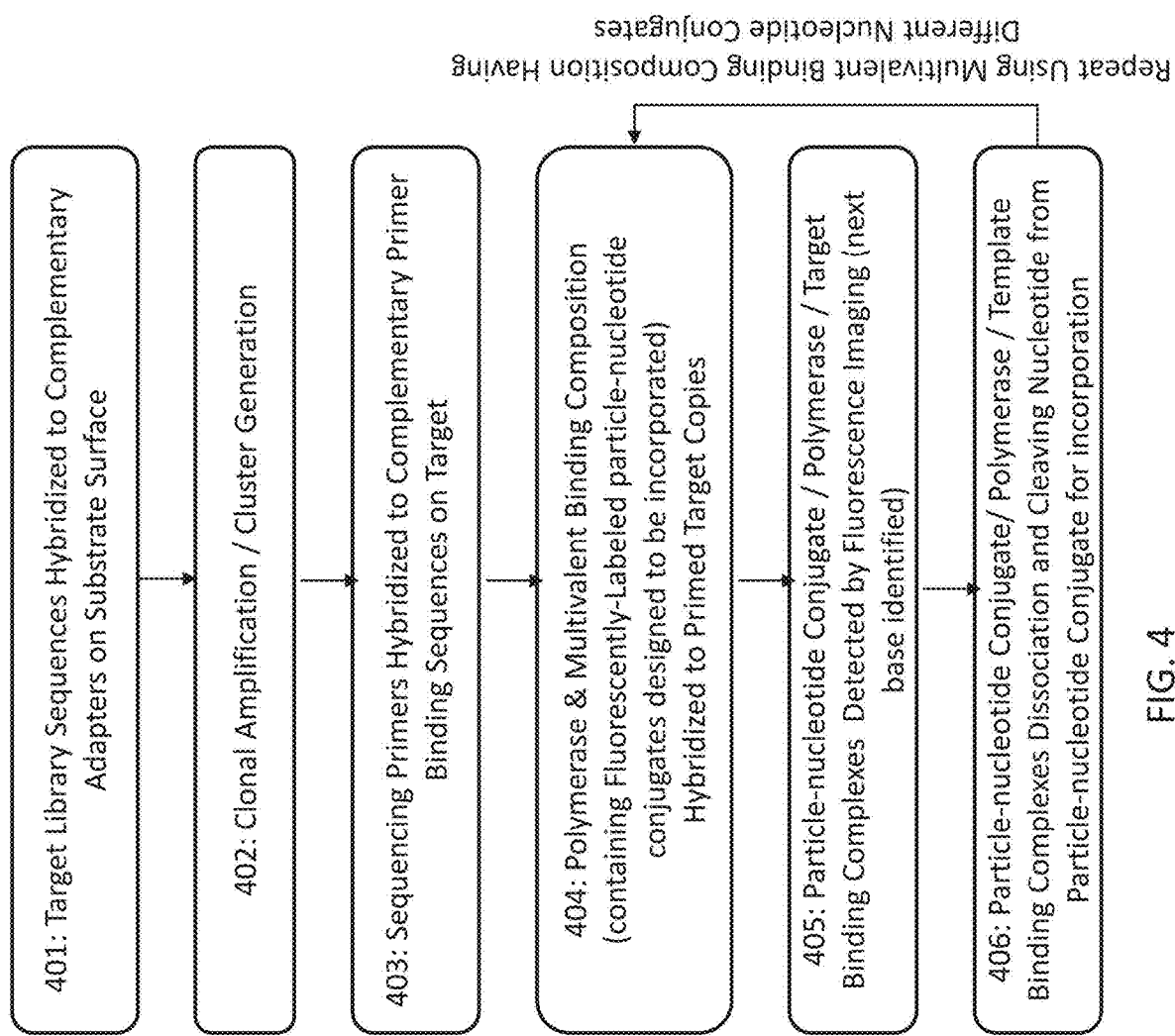
FIG. 4 shows a flow chart outlining the steps for sequencing a target nucleic acid and extending the primer strand through incorporating the nucleotide on the particle-nucleotide conjugate.

FIG. 4 is another flowchart outlining the steps in sequencing a target nucleic acid, which includes cleaving a nucleotide from the particle-nucleotide conjugate and incorporating the cleaved nucleotide. 401 describes a step of attaching target library sequences to a solid support surface by hybridizing the target nucleic acid molecules to complementary adapters on substrate surface. The target nucleic acid molecules can be single stranded or partially double stranded. Prior to 401, the nucleic acid molecules in the target library may have been prepared to contain fragments complementary to the adaptor sequences through ligation or other methods. 402 describes the step of clonal amplification to generate clusters of target nucleic acid molecules on the surface. 403 describes hybridizing sequencing primers to complementary primer binding sequences on the target nucleic acid to form the primed target nucleic acid. 404 describes combining the polymerase, the multivalent binding composition, which contains labeled (e.g., fluorescently-labeled) particle-nucleotide conjugates, and the primed target nucleic acid. In the particle-nucleotide conjugates, the nucleotides are attached to the particle through chemical bonds or interactions that can be later severed. 404 may also include a step of washing or removing the unbound reagents including polymerase and particle-nucleotide conjugate.

In 405, when the nucleotide on the particle-nucleotide conjugate is complementary to the next base of the primed target nucleic acid, the particle-nucleotide conjugate, polymerase, and primed target nucleic acid form a ternary binding complex, which can be detected by detection methods (e.g., florescence imaging) compatible with the label on the particle-nucleotide conjugate. 405 can also include measuring the persistence time of the ternary binding complex. In 406, the polymerase is placed in a condition that would make it catalytically active to incorporate a nucleotide. The condition can include exposing the polymerase to Mg or Mn ions in the reaction solution. The nucleotide that is bound to the polymerase and the primed target nucleic acid is then cleaved from the particle and then incorporated into the primed strand of the primed target nucleic acid. The binding complex is destabilized. 406 may also include a step of washing or removing the dissociated particle-nucleotide conjugate and/or polymerase. After the extension, steps 404, 405, and 406 can be repeated in multiple cycles to determine the sequences of the target nucleic acid.

B. Detecting Target Nucleic Acid

FIG. 4 illustrates one exemplified method in which the multivalent binding composition is used for detecting a target nuclei acid. As shown in FIG. 4A, the polymer-nucleotide conjugate 201 is placed in contact with polymerase 206, a first nucleic acid molecule 204 and a second nucleic acid molecule 205. The polymer-nucleotide conjugate 201 has multiple polymer branches radiating from the core, and some branches are attached to nucleotide or oligonucleotide 202, and some branches are attached to a label 203. When the nucleotide or oligonucleotide 202 on the polymer-nucleotide conjugate 201 is complementary to at least a fraction of the first nucleic acid 204, a binding complex is formed as shown in FIG. 4B, and the strong binding signal can helps detect target nucleic acid with sequences complementary or partially complementary to the nucleotide or oligonucleotide on the polymer-nucleotide conjugate. In some instances, at least one of the polymerase, nucleic acid molecules, and polymer-nucleotide conjugates is attached to a solid support.

The multivalent binding composition described herein can be used in a method of detecting a target nucleic acid in a sample. Also disclosed herein are systems configured for performing any of the disclosed nucleic acid analysis methods. The system may comprise a fluid flow controller and/or fluid dispensing system configured to sequentially and iteratively contact the nucleic acid molecules with the disclosed polymerase and multivalent binding compositions and/or reagents. The contacting may be performed within one or more flow cells. In some instances, said flow cells may be fixed components of the system. In some instances, said flow cells may be removable and/or disposable components of the system. The system may also include a cartridge comprising a sample collection unit and an assay assembly, wherein the sample collection unit is configured to collect a sample, and wherein the assay assembly comprises at least one reaction site containing a multivalent binding composition adapted to interact with said analyte, allowing the predetermined portion of sample to react with assay reagents contained within the assay assembly to yield a signal indicative of the presence of the analyte in the sample, and detecting the signal generated from the analyte.

III. Multivalent Binding Composition

The present disclosure relates to multivalent binding compositions having a plurality of nucleotides conjugated to a particle (e.g., a polymer, branched polymer, dendrimer, or equivalent structure). Contacting the multivalent binding composition with a polymerase and a primed target nucleic acid may result in the formation of a ternary complex which may be detected and in turn achieve a more accurate determination of the bases of the target nucleic acid.

When the multivalent binding composition is used in replacement of single unconjugated or untethered nucleotide to form a complex with the polymerase and the target nucleic acid, the local concentration of the nucleotide is increased many fold, which in turn enhances the signal intensity, particularly the correct signal versus mismatch. The multivalent binding composition described herein can include at least one particle-nucleotide conjugate for interacting with the target nucleic acid. The multivalent composition can also include two, three, or four different particle-nucleotide conjugates, each having a different nucleotide conjugated to the particle.

The multivalent binding composition can comprise 1, 2, 3, 4, or more types of particle-nucleotide conjugates, wherein each particle-nucleotide conjugate comprises a different type of nucleotide. A first type of the particle-nucleotide conjugate can comprise a nucleotide selected from the group consisting of ATP, ADP, AMP, dATP, dADP, and dAMP. A second type of the particle-nucleotide conjugate can comprise a nucleotide selected from the group consisting of TTP, TDP, TMP, dTTP, dTDP, dTMP, UTP, UDP, UMP, dUTP, dUDP, and dUMP. A third type of the particle-nucleotide conjugate can comprise a nucleotide selected from the group consisting of CTP, CDP, CMP, dCTP, dCDP, and dCMP. A fourth type of the particle-nucleotide conjugate can comprise a nucleotide selected from the group consisting of GTP, GDP, GMP, dGTP, dGDP, and dGMP. In some embodiments, each particle-nucleotide conjugate comprises a single type of nucleotide respectively corresponding to one or more nucleotide selected from the group consisting of ATP, ADP, AMP, dATP, dADP, dAMP TTP, TDP, TMP, dTTP, dTDP, dTMP, UTP, UDP, UMP, dUTP, dUDP, dUMP, CTP, CDP, CMP, dCTP, dCDP, dCMP, GTP, GDP, GMP, dGTP, dGDP, and dGMP. Each multivalent binding composition may further comprise one or more labels corresponding to the particular nucleotide conjugated to each respective conjugate. Exemplary labels include fluorescent labels, colorimetric labels, electrochemical labels (such as, for example, glucose or other reducing sugars, or thiols or other redox active moieties), luminescent labels, spin labels, radioactive labels, steric labels, affinity tags, or the like.

A. Particle-Nucleotide Conjugate

In a particle-nucleotide conjugate, multiple copies of the same nucleotide may be covalently bound to or noncovalently bound to the particle. Examples of the particle can include a branched polymer; a dendrimer; a cross linked polymer particle such as an agarose, polyacrylamide, acrylate, methacrylate, cyanoacrylate, methyl methacrylate particle; a glass particle; a ceramic particle; a metal particle; a quantum dot; a liposome; an emulsion particle, or any other particle (e.g, nanoparticles, microparticles, or the like) known in the art. In a preferred embodiment, the particle is a branched polymer.

The nucleotide can be linked to the particle through a linker, and the nucleotide can be attached to one end or location of a polymer. The nucleotide can be conjugated to the particle through the 5' end of the nucleotide. In some particle-nucleotide conjugates, one nucleotide attached to one end or location of a polymer. In some particle-nucleotide conjugate, multiple nucleotides are attached to one end or location of a polymer. The conjugated nucleotide is sterically accessible to one or more proteins, one or more enzymes, and nucleotide binding moieties. In some embodiments, a nucleotide may be provided separately from a nucleotide binding moiety such as a polymerase. In some embodiments, the linker does not comprise a photo emitting or photo absorbing group.

The particle can also have a binding moiety. In some embodiments, particles may self-associate without the use of a separate interaction moiety. In some embodiments, particles may self-associate due to buffer conditions or salt conditions, e.g., as in the case of calcium-mediated interactions of hydroxyapatite particles, lipid or polymer mediated interactions of micelles or liposomes, or salt-mediated aggregation of metallic (such as iron or gold) nanoparticles.

The particle-nucleotide conjugate can have one or more labels. Examples of the labels include but are not limited to fluorophores, spin labels, metals or metal ions, colorimetric labels, nanoparticles, PET labels, radioactive labels, or other such label as may render said composition detectable by such methods as are known in the art of the detection of macromolecules or molecular interactions. The label may be attached to the nucleotide (e.g. by attachment to the 5' phosphate moiety of a nucleotide), to the particle itself (e.g., to the PEG subunits), to an end of the polymer, to a central moiety, or to any other location within said polymer-nucleotide conjugate which would be recognized by one of skill in the art to be sufficient to render said composition, such as a particle, detectable by such methods as are known in the art or described elsewhere herein. In some embodiments, one or more labels are provided so as to correspond to or differentiate a particular particle-nucleotide conjugate.

In some embodiments, the label is a fluorophore. Exemplary fluorescent moieties include, but are not limited to, fluorescein and fluorescein derivatives such as carboxyfluorescein, tetrachlorofluorescein, hexachlorofluorescein, carboxynapthofluorescein, fluorescein isothiocyanate, NHS-fluorescein, iodoacetamidofluorescein, fluorescein maleimide, SAMSA-fluorescein, fluorescein thiosemicarbazide, carbohydrazinomethylthioacetyl-amino fluorescein, rhodamine and rhodamine derivatives such as TRITC, TMR, lissamine rhodamine, Texas Red, rhodamine B, rhodamine 6G, rhodamine 10, NHS-rhodamine, TMR-iodoacetamide, lissamine rhodamine B sulfonyl chloride, lissamine rhodamine B sulfonyl hydrazine, Texas Red sulfonyl chloride, Texas Red hydrazide, coumarin and coumarin derivatives such as AMCA, AMCA-NHS, AMCA-sulfo-NHS, AMCA-HPDP, DCIA, AMCE-hydrazide, BODIPY and derivatives such as BODIPY FL C3-SE, BODIPY 530/550 C3, BODIPY 530/550 C3-SE, BODIPY 530/550 C3 hydrazide, BODIPY 493/503 C3 hydrazide, BODIPY FL C3 hydrazide, BODIPY FL IA, BODIPY 530/551 IA, Br-BODIPY 493/503, Cascade Blue and derivatives such as Cascade Blue acetyl azide, Cascade Blue cadaverine, Cascade Blue ethylenediamine, Cascade Blue hydrazide, Lucifer Yellow and derivatives such as Lucifer Yellow iodoacetamide, Lucifer Yellow CH, cyanine and derivatives such as indolium based cyanine dyes, benzo-indolium based cyanine dyes, pyridium based cyanine dyes, thiozolium based cyanine dyes, quinolinium based cyanine dyes, imidazolium based cyanine dyes, Cy 3, Cy5, lanthanide chelates and derivatives such as BCPDA, TBP, TMT, BHHCT, BCOT, Europium chelates, Terbium chelates, Alexa Fluor dyes, DyLight dyes, Atto dyes, LightCycler Red dyes, CAL Flour dyes, JOE and derivatives thereof, Oregon Green dyes, WellRED dyes, IRD dyes, phycoerythrin and phycobilin dyes, Malachite green, stilbene, DEG dyes, NR dyes, near-infrared dyes and others known in the art such as those described in Haugland, Molecular Probes Handbook, (Eugene, Oreg.) 6th Edition; Lakowicz, Principles of Fluorescence Spectroscopy, 2nd Ed., Plenum Press New York (1999), or Hermanson, Bioconjugate Techniques, 2nd Edition, or derivatives thereof, or any combination thereof. Cyanine dyes may exist in either sulfonated or non-sulfonated forms, and consist of two indolenin, benzo-indolium, pyridium, thiozolium, and/or quinolinium groups separated by a polymethine bridge between two nitrogen atoms. Commercially available cyanine fluorophores include, for example, Cy3, (which may comprise 1-[6-(2,5-dioxopyrrolidin-1-yloxy)-6-oxohexyl]-2-(3-1-[6-(2,5-dioxopyrrolidin-1-yloxy)-6-oxohexyl]-3,3- dimethyl-1,3-dihydro-2H-indol-2-ylidene}prop-1-en-1-yl)-3,3-dimethyl-3H-indolium or 1-[6-(2,5-dioxopyrrolidin-1-yloxy)-6-oxohexyl]-2-(3-{1-[6-(2,5-dioxopyrrolidin-1-yloxy)-6-oxohexyl]-3,3-dimethyl-5-sulfo-1,3-dihydro-2H-indol-2-ylidene}prop-1-en-1-yl)-3,3-dimethyl-3H-indolium-5-sulfonate), Cy5 (which may comprise 1-(6-((2,5-dioxopyrrolidin-1-yl)oxy)-6-oxohexyl)-2-((1E,3E)-5-((E)-1-(6-((2,5-dioxopyrrolidin-1-yl)oxy)-6-oxohexyl)-3,3-dimethyl-5-indolin-2-ylidene)penta-1,3-dien-1-yl)-3,3-dimethyl-3H-indol-1-ium or 1-(6-((2,5-dioxopyrrolidin-1-yl)oxy)-6-oxohexyl)-2-((1E,3E)-5-((E)-1-(6-((2,5-dioxopyrrolidin-1-yl)oxy)-6-oxohexyl)-3,3-dimethyl-5-sulfoindolin-2-ylidene)penta-1,3-dien-1-yl)-3,3-dimethyl-3H-indol-1-ium-5-sulfonate), and Cy7 (which may comprise 1-(5-carboxypentyl)-2-[(1E,3E,5E,7Z)-7-(1-ethyl-1,3-dihydro-2H-indol-2-ylidene)hepta-1,3,5-trien-1-yl]-3H-indolium or 1-(5-carboxypentyl)-2-[(1E,3E,5E,7Z)-7-(1-ethyl-5-sulfo-1,3-dihydro-2H-indol-2-ylidene)hepta-1,3,5-trien-1-yl]-3H-indolium-5-sulfonate), where "Cy" stands for 'cyanine', and the first digit identifies the number of carbon atoms between two indolenine groups. Cy2 which is an oxazole derivative rather than indolenin, and the benzo-derivatized Cy3.5, Cy5.5 and Cy7.5 are exceptions to this rule.

In some embodiments, the detection label can be a FRET pair, such that multiple classifications can be performed under a single excitation and imaging step. As used herein, FRET may comprise excitation exchange (Forster) transfers, or electron-exchange (Dexter) transfers.

B. Polymer-Nucleotide Conjugate

Figure 5:
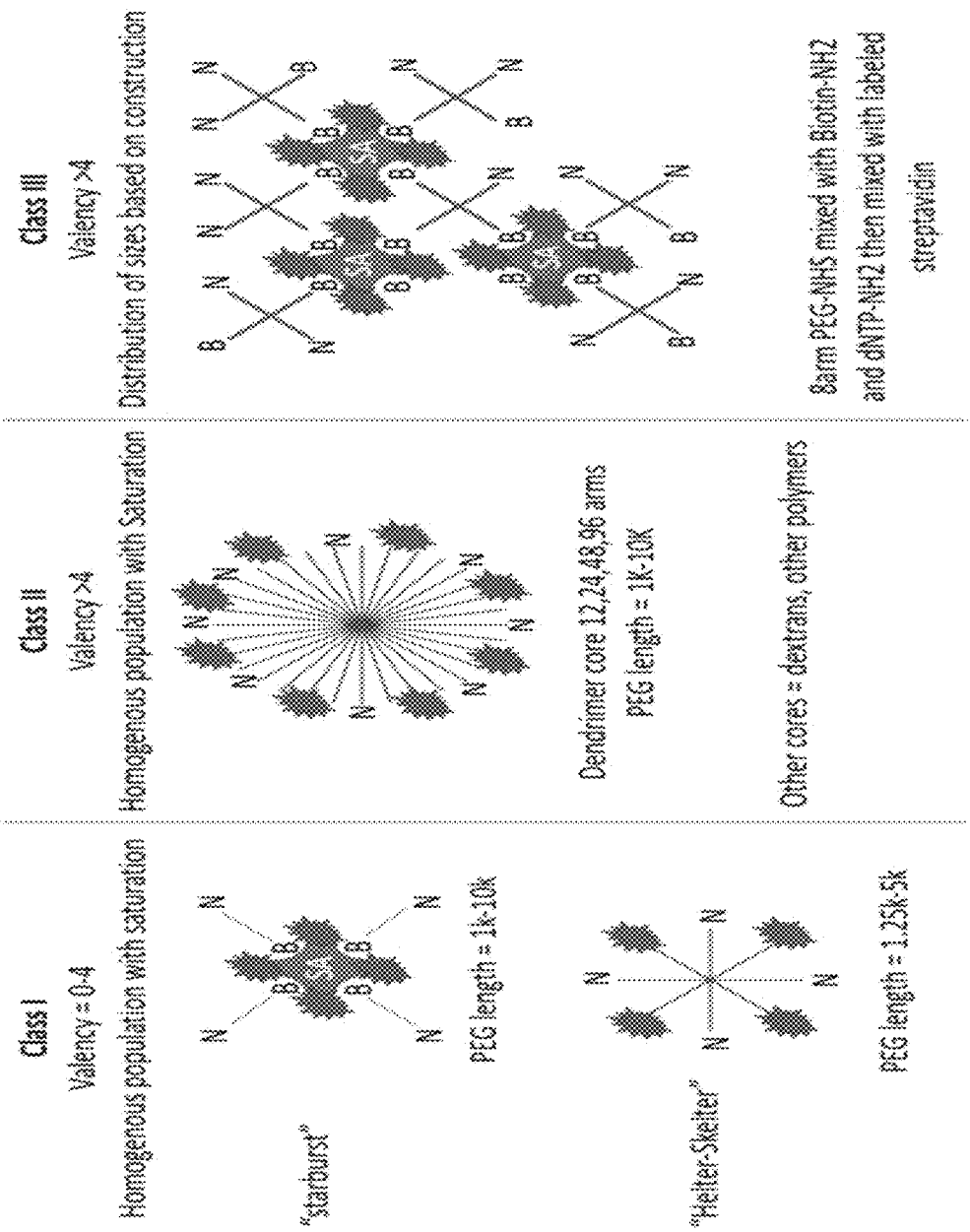
FIG. 5A-5C shows schematic representations of non-limiting examples of varying configurations of the polymer-nucleotide conjugates.

One example of the particle-nucleotide conjugate is a polymer-nucleotide conjugate. Some non-limiting examples of the polymer-nucleotide conjugates are shown in FIG. 5A-5C. For example, FIG. 5A shows polymer-nucleotide conjugates having various configurations; FIG. 5B shows a polymer-nucleotide conjugate having the polymer branch radiating from the center; and FIG. 5C shows polymer-nucleotide conjugates having a binding moiety such as a biotin.

Examples of the branched polymer include polyethylene glycol (PEG), polypropylene glycol, polyvinyl alcohol, polylactic acid, polyglycolic acid, polyglycine, polyvinyl acetate, a dextran, or other such polymers, or copolymers incorporating any two or more of the foregoing or incorporating other polymers as are known in the art. In one embodiment, the polymer is a PEG. In another embodiment, the polymer can have PEG branches.

Suitable polymers may be characterized by a repeating unit incorporating a functional group suitable for derivatization such as an amine, a hydroxyl, a carbonyl, or an allyl group. The polymer can also have one or more pre-derivatized substituents such that one or more particular subunits will incorporate a site of derivatization or a branch site, whether or not other subunits incorporate the same site, substituent, or moiety. A pre-derivatized substituent may comprise or may further comprise, for example, a nucleotide, a nucleoside, a nucleotide analog, a label such as a fluorescent label, radioactive label, or spin label, an interaction moiety, an additional polymer moiety, or the like, or any combination of the foregoing.

In the polymer-nucleotide conjugate, the polymer can have a plurality of branches. The branched polymer can have various configurations, including but are not limited to stellate ("starburst") forms, aggregated stellate ("helter skelter") forms, bottle brush, or dendrimer. The branched polymer can radiate from a central attachment point or central moiety, or may incorporate multiple branch points, such as, for example, 2, 3, 4, 5, 6, 7, 8, 9, 10, or more branch points. In some embodiments, each subunit of a polymer may optionally constitute a separate branch point.

The length and size of the branch can differ based on the type of polymer. In some branched polymers, the branch may have a length of between 1 and 1,000 nm, between 1 and 100 nm, between 1 and 200 nm, between 1 and 300 nm, between 1 and 400 nm, between 1 and 500 nm, between 1 and 600 nm, between 1 and 700 nm, between 1 and 800 nm, or between 1 and 900 nm, or more, or having a length falling within or between any of the values disclosed herein. In some branched polymers, the branch may have a size corresponding to an apparent molecular weight of 1K, 2K, 3K, 4K, 5K, 10K, 15K, 20K, 30K, 50K, 80K, 100K, or any value within a range defined by any two of the foregoing. The apparent molecular weight of a polymer may be calculated from the known molecular weight of a representative number of subunits, as determined by size exclusion chromatography, as determined by mass spectrometry, or as determined by any other method as is known in the art. The polymer can have multiple branches. The number of branches in the polymer can be 2, 3, 4, 5, 6, 7, 8, 12, 16, 24, 32, 64, 128 or more, or a number falling within a range defined by any two of these values.

For the polymer-nucleotide conjugate, the branched polymer of 4, 8, 16, 32, or 64 branches can have nucleotides attached to the ends of PEG branches, such that each end has attached thereto 0, 1, 2, 3, 4, 5, 6 or more nucleotides. In one non-limiting example, the branched polymer of between 3 and 128 PEG arms having attached to the polymer branches ends one or more nucleotides, such that each end has attached thereto 0, 1, 2, 3, 4, 5, 6 or more nucleotides or nucleotide analogs. In some embodiments, a branched polymer or dendrimer has an even number of arms. In some embodiments, a branched polymer or dendrimer has an odd number of arms.

In the polymer-nucleotide conjugate, each branch or a subset of branches of the polymer may have attached thereto a moiety comprising a nucleotide (e.g., an adenine, a thymine, a uracil, a cytosine, or a guanine residue or a derivative or mimetic thereof), and the moiety is capable of binding to a polymerase, reverse transcriptase, or other nucleotide binding domain. Optionally, the moiety may be capable of being incorporated into an elongating nucleic acid chain during a polymerase reaction. In some instances, said moiety may be blocked such that it is not capable of being incorporated into an elongating nucleic acid chain during a polymerase reaction. In some other instances, said moiety may be reversibly blocked such that it is not capable of being incorporated into an elongating nucleic acid chain during a polymerase reaction until such block is removed, after which said moiety is then capable of being incorporated into an elongating nucleic acid chain during a polymerase reaction.

The nucleotide can be conjugated to the polymer branch through the 5' end of the nucleotide. In some instances, the nucleotide may be modified so as to inhibit or prevent incorporation of the nucleotide into an elongating nucleic acid chain during a polymerase reaction. By way of example, the nucleotide may include a 3' deoxyribonucleotide, a 3' azidonucleotide, a 3'-methyl azido nucleotide, or another such nucleotide as is or may be known in the art, so as to not be capable of being incorporated into an elongating nucleic acid chain during a polymerase reaction. In some embodiments, the nucleotide can include a 3'-O-azido group, a 3'-O-azidomethyl group, a 3'-phosphorothioate group, a 3'-O-malonyl group, a 3'-O-alkyl hydroxylamino group, or a 3'-O-benzyl group. In some embodiments, the nucleotide lacks a 3' hydroxyl group.

The polymer can further have a binding moiety in each branch or a subset of branches. Some examples of the binding moiety include but are not limited to biotin, avidin, strepavidin or the like, polyhistidine domains, complementary paired nucleic acid domains, G-quartet forming nucleic acid domains, calmodulin, maltose-binding protein, cellulase, maltose, sucrose, glutathione-S-transferase, glutathione, O-6-methylguanine-DNA methyltransferase, benzylguanine and derivatives thereof, benzylcysteine and derivatives thereof, an antibody, an epitope, a protein A, a protein G. The binding moiety can be any interactive molecules or fragment thereof known in the art to bind to or facilitate interactions between proteins, between proteins and ligands, between proteins and nucleic acids, between nucleic acids, or between small molecule interaction domains or moieties.

In some embodiments, a composition as provided herein may comprise one or more elements of a complementary interaction moiety. Exemplary complementary interaction moieties include, for example, biotin and avidin; SNAP-benzylguanosine; antibody or FAB and epitope; IgG FC and Protein A, Protein G, ProteinA/G, or Protein L; maltose binding protein and maltose; lectin and cognate polysaccharide; ion chelation moieties, complementary nucleic acids, nucleic acids capable of forming triplex or triple helical interactions; nucleic acids capable of forming G-quartets, and the like. One of skill in the art will readily recognize that many pairs of moieties exist and are commonly used for their property of interacting strongly and specifically with one another; and thus any such complementary pair or set is considered to be suitable for this purpose in constructing or envisioning the compositions of the present disclosure. In some embodiments, a composition as disclosed herein may comprise compositions in which one element of a complementary interaction moiety is attached to one molecule or multivalent ligand, and the other element of the complementary interaction moiety is attached to a separate molecule or multivalent ligand. In some embodiments, a composition as disclosed herein may comprise compositions in which both or all elements of a complementary interaction moiety are attached to a single molecule or multivalent ligand. In some embodiments, a composition as disclosed herein may comprise compositions in which both or all elements of a complementary interaction moiety are attached to separate arms of, or locations on, a single molecule or multivalent ligand. In some embodiments, a composition as disclosed herein may comprise compositions in which both or all elements of a complementary interaction moiety are attached to the same arm of, or locations on, a single molecule or multivalent ligand. In some embodiments, compositions comprising one element of a complementary interaction moiety and compositions comprising another element of a complementary interaction moiety may be simultaneously or sequentially mixed. In some embodiments, interactions between molecules or particles as disclosed herein allow for the association or aggregation of multiple molecules or particles such that, for example, detectable signals are increased. In some embodiments, fluorescent, colorimetric, or radioactive signals are enhanced. In other embodiments, other interaction moieties as disclosed herein or as are known in the art are contemplated. In some embodiments, a composition as provided herein may be provided such that one or more molecules comprising a first interaction moiety such as, for example, one or more imidazole or pyridine moieties, and one or more additional molecules comprising a second interaction moiety such as, for example, histidine residues, are simultaneously or sequentially mixed. In some embodiments, said composition comprises 1, 2, 3, 4, 5, 6, or more imidazole or pyridine moieties. In some embodiments, said composition comprises 1, 2, 3, 4, 5, 6, or more histidine residues. In such embodiments, interaction between the molecules or particles as provided may be facilitated by the presence of a divalent cation such as nickel, manganese, magnesium, calcium, strontium, or the like. In some embodiments, for example, a $(His)_3$ group may interact with a $(His)_3$ group on another molecule or particle via coordination of a nickel or manganese ion.

The multivalent binding composition may comprise one or more buffers, salts, ions, or additives. In some embodiments, representative additives may include, but are not limited to, betaine, spermidine, detergents such as Triton X-100, Tween 20, SDS, or NP-40, ethylene glycol, polyethylene glycol, dextran, polyvinyl alcohol, vinyl alcohol, methylcellulose, heparin, heparan sulfate, glycerol, sucrose, 1,2-propanediol, DMSO, N,N,N-trimethylglycine, ethanol, ethoxyethanol, propylene glycol, polypropylene glycol, block copolymers such as the Pluronic (r) series polymers, arginine, histidine, imidazole, or any combination thereof, or any substance known in the art as a DNA "relaxer" (a compound, with the effect of altering the persistence length of DNA, altering the number of within-polymer junctions or crossings, or altering the conformational dynamics of a DNA molecule such that the accessibility of sites within the strand to DNA binding moieties is increased).

The multivalent binding composition may include zwitterionic compounds as additives. Further representative additives may be found in Lorenz, T. C. J. Vis. Exp. (63), e3998, doi:10.3791/3998 (2012), which is hereby incorporated by reference with respect to its disclosure of additives for the facilitation of nucleic acid binding or dynamics, or the facilitation of processes involving the manipulation, use, or storage of nucleic acids. In some embodiments, representative cations may include, but are not limited to, sodium, magnesium, strontium, potassium, manganese, calcium, lithium, nickel, cobalt, or other such cations as are known in the art to facilitate nucleic acid interactions, such as self-association, secondary or tertiary structure formation, base pairing, surface association, peptide association, protein binding, or the like.

IV. Binding Between Target Nucleic Acid and Multivalent Binding Composition

When the multivalent binding composition is used in replacement of single unconjugated or untethered nucleotide to form a complex with the polymerase and the target nucleic acid, the local concentration of the nucleotide is increased many folds, which in turn enhances the signal intensity, particularly the correct signal versus mismatch. The present disclosure contemplates contacting the multivalent binding composition with a polymerase and a primed target nucleic acid to determine the formation of a ternary binding complex.

Figure 6:
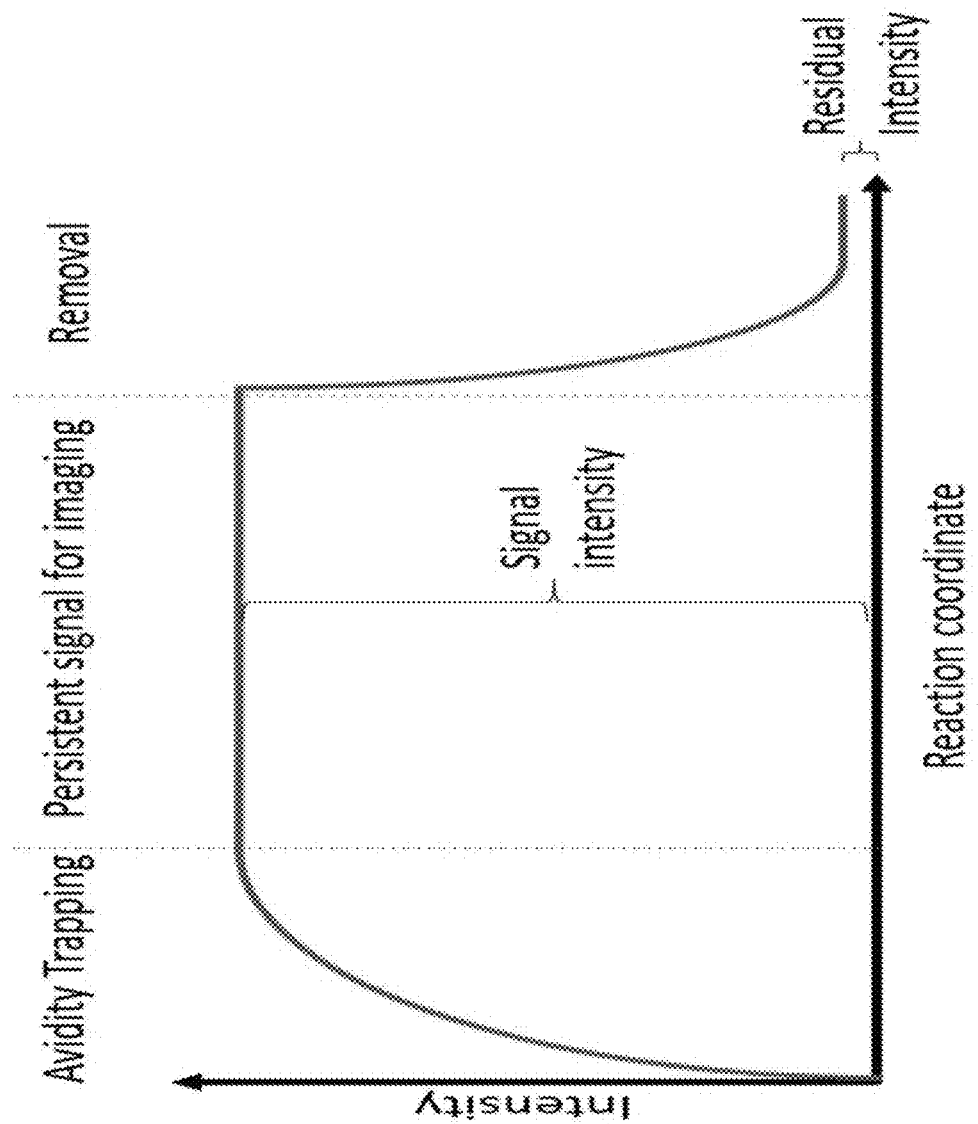
FIG. 6 shows a generalized graphical depiction of the increase in signal intensity that has been observed during binding, persistence, and washing and removal of multivalent substrates.

FIG. 6 has demonstrated the use of the polymer-nucleotide conjugate increased the signal intensity during binding, persistence, and washing/removal steps. Because of the increased local concentration of the nucleotide on the polymer-nucleotide conjugate, the binding between the polymerase, the primed target strand, and the nucleotide, when the nucleotide is complementary to the next base of the target nucleic acid, becomes more favorable. The formed binding complex has a longer persistence time which in turn helps shorten the imaging step. The high signal intensity resulted from the use of the polymer nucleotide conjugate remain for the entire binding and imaging step. The strong binding between the polymerase, the primed target strand, and the nucleotide or nucleotide analog also means that the formed binding complex will remain stabilized during the washing step and the signal will remain at a high intensity when other reaction mixture and unmatched nucleotide analogs are washed away. After the imaging step, the binding complex can be destabilized and the primed target nucleic acid can then be extended for one base. After the extension, the binding and imaging steps can be repeated again with the use of the polymer nucleotide conjugate to determine the identity of the next base.

As an example, a graphical depiction of the increase in signal intensity during binding, persistence, and washing/removal of a multivalent substrate as described herein is provided in FIG. 10, which is representative of the changes in signal intensity that have been observed experimentally. Therefore, the compositions and methods of the present disclosure provide a robust and controllable means of establishing and maintaining a ternary enzyme complex, as well as providing vastly improved means by which the presence of said complex may be identified and/or measured, and a means by which the persistence of said complex may be controlled. This provides important solutions to problems such as that of determining the identity of the N+1 base in nucleic acid sequencing applications.

Without intending to be bound by any particular theory, it has been observed that multivalent binding compositions disclosed herein associate with polymerase nucleotide complexes in order to form a ternary binding complexes with a rate that is time-dependent, though substantially slower than the rate of association known to be obtainable by nucleotides in free solution. Thus, the on-rate (Kon) is substantially and surprisingly slower than the on rate for single nucleotides or nucleotides not attached to multivalent ligand complexes. Importantly, however, the off rate (Koff) of the multivalent ligand complex is substantially slower than that observed for nucleotides in free solution. Therefore, the multivalent ligand complexes of the present disclosure provide a surprising and beneficial improvement of the persistence of ternary polymerase-polynucleotide-nucleotide complexes (especially over such complexes that are formed with free nucleotides) allowing, for example, significant improvements in imaging quality for nucleic acid sequencing applications, over currently available methods and reagents. Importantly, this property of the multivalent substrates disclosed herein renders the formation of visible ternary complexes controllable, such that subsequent visualization, modification, or processing steps may be undertaken essentially without regard to the dissociation of the complex—that is, the complex can be formed, imaged, modified, or used in other ways as necessary, and will remain stable until a user carries out an affirmative dissociation step, such as exposing the complexes to a dissociation buffer.

In various embodiments, polymerases suitable for the binding interaction describe herein include may include any polymerase as is or may be known in the art. It is, for example, known that every organism encodes within its genome one or more DNA polymerases. Exemplary polymerases may include but are not limited to: Klenow DNA polymerase, *Thermus aquaticus* DNA polymerase I (Taq polymerase), KlenTaq® polymerase, and bacteriophage T7 DNA polymerase; human alpha, delta and epsilon DNA polymerases; bacteriophage polymerases such as T4, RB69 and phi29 bacteriophage DNA polymerases, *Pyrococcus furiosus* DNA polymerase (Pfu polymerase); *Bacillus subtilis* DNA polymerase III, and *E. coli* DNA polymerase III alpha and epsilon; 9 degree N polymerase, reverse transcriptases such as HIV type M or O reverse transcriptases, avian myeloblastosis virus reverse transcriptase, or Moloney Murine Leukemia Virus (MMLV) reverse transcriptase, or telomerase. Further non-limiting examples of DNA polymerases can include those from various Archaea genera, such as, *Aeropyrum, Archaeglobus, Desulfurococcus, Pyrobaculum, Pyrococcus, Pyrolobus, Pyrodictium, Staphylothermus, Stetteria, Sulfolobus, Thermococcus,* and *Vulcanisaeta* and the like or variants thereof, including such polymerases as are known in the art such as Vent™, Deep Vent™, Pfu, KOD, Pfx, Terminator™, and Tgo polymerases. In some embodiments, the polymerase is a klenow polymerase.

The ternary complex has longer persistence time when the nucleotide on the polymer-nucleotide conjugate is complementary to the target nucleic acid than when a non-complementary nucleotide. The ternary complex also has longer persistence time when the nucleotide on the polymer-nucleotide conjugate is complementary to the target nucleic acid than a complementary nucleotide that is not conjugated or tethered. For example, in some embodiments, said ternary complexes may have a persistence time of less than 1 s, greater than 1 s, greater than 2 s, greater than 3 s, greater than 5 s, greater than 10 s, greater than 15 s, greater than 20 s, greater than 30 s, greater than 60 s, greater than 120 s, greater than 360 s, greater than 3600 s, or more, or for a time lying within a range defined by any two or more of these values.

The persistence time can be measured, for example, by observing the onset and/or duration of a binding complex, such as by observing a signal from a labeled component of the binding complex. For example, a labeled nucleotide or a labeled reagent comprising one or more nucleotides may be present in a binding complex, thus allowing the signal from the label to be detected during the persistence time of the binding complex.

It has been observed that different ranges of persistence times are achievable with different salts or ions, showing, for example, that complexes formed in the presence of, for example, Mg form more quickly than complexes formed with other ions. It has also been observed that complexes formed in the presence of, for example, Sr, form readily and dissociate completely or with substantial completeness upon withdrawal of the ion or upon washing with buffer lacking one or more components of the present compositions, such as, e.g., a polymer and/or one or more nucleotides, and/or one or more interaction moieties, or a buffer containing, for example, a chelating agent which may cause or accelerate the removal of a divalent cation from the multivalent reagent containing complex. Thus, in some embodiments, a composition of the present disclosure comprises Mg. In some embodiments, a composition of the present disclosure comprises Ca. In some embodiments, a composition of the present disclosure comprises Sr. In some embodiments, a composition of the present disclosure comprises Co. In some embodiments, a composition of the present disclosure comprises $MgCl_2$. In some embodiments, a composition of the present disclosure comprises $CaCl_2$). In some embodiments, a composition of the present disclosure comprises $SrCl_2$. In some embodiments, a composition of the present disclosure comprises Co $Cl_2$. In some embodiments, the composition comprises no, or substantially no Magnesium. In some embodiments, the composition comprises no, or substantially no Calcium. In some embodiments, the methods of the present disclosure provide for the contacting of one or more nucleic acids with one or more of the compositions disclosed herein wherein said composition lacks either one of calcium or magnesium, or lacks both calcium or magnesium.

The dissociation of ternary complexes can be controlled by changing the buffer conditions. After the imaging step, a buffer with increased salt content is used to cause dissociation of the ternary complexes such that labeled polymer-nucleotide conjugates can be washed out, providing a means by which signals can be attenuated or terminated, such as in the transition between one sequencing cycle and the next. This dissociation may be effected, in some embodiments, by washing the complexes with a buffer lacking a necessary metal or cofactor. In some embodiments, a wash buffer may comprise one or more compositions for the purpose of maintaining pH control. In some embodiments, a wash buffer may comprise one or more monovalent cations, such as sodium. In some embodiments, a wash buffer lacks or substantially lacks a divalent cation, for example, having no or substantially no strontium, calcium, magnesium, or manganese. In some embodiments, a wash buffer further comprises a chelating agent, such as, for example, EDTA, EGTA, nitrilotriacetic acid, polyhistidine, imidazole, or the like. In some embodiments, a wash buffer may maintain the pH of the environment at the same level as for the bound complex. In some embodiments, a wash buffer may raise or lower the pH of the environment relative to the level seen for the bound complex. In some embodiments, the pH may be within a range from 2-4, 2-7, 5-8, 7-9, 7-10, or lower than 2, or higher than 10, or a range defined by any two of the values provided herein.

Addition of a particular ion may affect the binding of the polymerase to a primed target nucleic acid, the formation of a ternary complex, the dissociation of a ternary complex, or the incorporation of one or more nucleotides into an elongating nucleic acid such as during a polymerase reaction. In some embodiments, relevant anions may comprise chloride, acetate, gluconate, sulfate, phosphate, or the like. In some embodiments, an ion may be incorporated into the compositions of the present disclosure by the addition of one or more acids, bases, or salts, such as $NiCl_2$, $CoCl_2$, $MgCl_2$, $MnCl_2$, $SrCl_2$, $CaCl_2$), $CaSO_4$, $SrCO_3$, $BaCl_2$ or the like. Representative salts, ions, solutions and conditions may be found in Remington: The Science and Practice of Pharmacy, 20th. Edition, Gennaro, A. R., Ed. (2000), which is hereby incorporated by reference in its entirety, and especially with respect to Chapter 17 and related disclosure of salts, ions, salt solutions, and ionic solutions.

The present disclosure contemplates contacting the multivalent binding composition comprising at least one particle-nucleotide conjugate with one or more polymerases. The contacting can be optionally done in the presence of one or more target nucleic acids. In some embodiments, said target nucleic acids are single stranded nucleic acids. In some embodiments, said target nucleic acids are primed single stranded nucleic acids. In some embodiments, said target nucleic acids are double stranded nucleic acids. In some embodiments, said contacting comprises contacting the multivalent binding composition with one polymerase. In some embodiments, said contacting comprises the contacting of said composition comprising one or more nucleotides with multiple polymerases. The polymerase can be bound to a single nucleic acid molecule.

The binding between target nucleic acid and multivalent binding composition may be provided in the presence of a polymerase that has been rendered catalytically inactive. In one embodiment, the polymerase may have been rendered catalytically inactive by mutation. In one embodiment, the polymerase may have been rendered catalytically inactive by chemical modification. In some embodiments, the polymerase may have been rendered catalytically inactive by the absence of a necessary substrate, ion, or cofactor. In some embodiments, the polymerase enzyme may have been rendered catalytically inactive by the absence of magnesium ions.

The binding between target nucleic acid and multivalent binding composition occur in the presence of a polymerase wherein the binding solution, reaction solution, or buffer lacks magnesium or manganese. Alternatively, the binding between target nucleic acid and multivalent binding composition occur in the presence of a polymerase wherein the binding solution, reaction solution, or buffer comprises calcium or strontium.

When the catalytically inactive polymerases are used to help a nucleic acid interact with a multivalent binding composition, the interaction between said composition and said polymerase stabilizes a ternary complex so as to render the complex detectable by fluorescence or by other methods as disclosed herein or otherwise known in the art. Unbound polymer-nucleotide conjugates may optionally be washed away prior to detection of the ternary binding complex.

Contacting of one or more nucleic acids with the polymer-nucleotide conjugates disclosed herein in a solution containing either one of calcium or magnesium, or containing both calcium and magnesium. Alternatively, the contacting of one or more nucleic acids with the polymer-nucleotide conjugates disclosed herein in a solution lacking either one of calcium or magnesium, or lacking both calcium or magnesium, and in a separate step, without regard to the order of the steps, adding to the solution one of calcium or magnesium, or both calcium and magnesium. In some embodiments, the contacting of one or more nucleic acids with the polymer-nucleotide conjugates disclosed herein in a solution lacking strontium, and comprises in a separate step, without regard to the order of the steps, adding to the solution strontium.

V. Use of Multivalent Binding Composition in Combination with Low Non-Specific Binding Surface Disclosed herein are solid supports comprising low non-specific binding surface compositions that enable improved nucleic acid hybridization and amplification performance. In general, the disclosed supports may comprise a substrate (or support structure), one or more layers of a covalently or non-covalently attached low-binding, chemical modification layers, e.g., silane layers, polymer films, and one or more covalently or non-covalently attached primer sequences that may be used for tethering single-stranded target nucleic acid(s) to the support surface. In some instances, the formulation of the surface, e.g., the chemical composition of one or more layers, the coupling chemistry used to cross-link the one or more layers to the support surface and/or to each other, and the total number of layers, may be varied such that non-specific binding of proteins, nucleic acid molecules, and other hybridization and amplification reaction components to the support surface is minimized or reduced relative to a comparable monolayer. Often, the formulation of the surface may be varied such that non-specific hybridization on the support surface is minimized or reduced relative to a comparable monolayer. The formulation of the surface may be varied such that non-specific amplification on the support surface is minimized or reduced relative to a comparable monolayer. The formulation of the surface may be varied such that specific amplification rates and/or yields on the support surface are maximized. Amplification levels suitable for detection are achieved in no more than 2, 3, 4, 5, 6, 7, 8, 9, 10, 15, 20, 25, 30, or more than 30 amplification cycles in some cases disclosed herein.

Examples of materials from which the substrate or support structure may be fabricated include, but are not limited to, glass, fused-silica, silicon, a polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET)), or any combination thereof. Various compositions of both glass and plastic substrates are contemplated.

The substrate or support structure may be rendered in any of a variety of geometries and dimensions known to those of skill in the art, and may comprise any of a variety of materials known to those of skill in the art. For example, in some instances the substrate or support structure may be locally planar (e.g., comprising a microscope slide or the surface of a microscope slide). Globally, the substrate or support structure may be cylindrical (e.g., comprising a capillary or the interior surface of a capillary), spherical (e.g., comprising the outer surface of a non-porous bead), or irregular (e.g., comprising the outer surface of an irregularly-shaped, non-porous bead or particle). In some instances, the surface of the substrate or support structure used for nucleic acid hybridization and amplification may be a solid, non-porous surface. In some instances, the surface of the substrate or support structure used for nucleic acid hybridization and amplification may be porous, such that the coatings described herein penetrate the porous surface, and nucleic acid hybridization and amplification reactions performed thereon may occur within the pores.

The substrate or support structure that comprises the one or more chemically-modified layers, e.g., layers of a low non-specific binding polymer, may be independent or integrated into another structure or assembly. For example, in some instances, the substrate or support structure may comprise one or more surfaces within an integrated or assembled microfluidic flow cell. The substrate or support structure may comprise one or more surfaces within a microplate format, e.g., the bottom surface of the wells in a microplate. As noted above, in some preferred embodiments, the substrate or support structure comprises the interior surface (such as the lumen surface) of a capillary. In alternate preferred embodiments the substrate or support structure comprises the interior surface (such as the lumen surface) of a capillary etched into a planar chip.

As noted, the low non-specific binding supports of the present disclosure exhibit reduced non-specific binding of proteins, nucleic acids, and other components of the hybridization and/or amplification formulation used for solid-phase nucleic acid amplification. The degree of non-specific binding exhibited by a given support surface may be assessed either qualitatively or quantitatively. For example, in some instances, exposure of the surface to fluorescent dyes (e.g., cyanins such as Cy3, or Cy5, etc., fluoresceins, coumarins, rhodamines, etc. or other dyes disclosed herein), fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a qualitative tool for comparison of non-specific binding on supports comprising different surface formulations. In some instances, exposure of the surface to fluorescent dyes, fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a quantitative tool for comparison of non-specific binding on supports comprising different surface formulations—provided that care has been taken to ensure that the fluorescence imaging is performed under conditions where fluorescence signal is linearly related (or related in a predictable manner) to the number of fluorophores on the support surface (e.g., under conditions where signal saturation and/or self-quenching of the fluorophore is not an issue) and suitable calibration standards are used. In some instances, other techniques known to those of skill in the art, for example, radioisotope labeling and counting methods may be used for quantitative assessment of the degree to which non-specific binding is exhibited by the different support surface formulations of the present disclosure.

Some surfaces disclosed herein exhibit a ratio of specific to nonspecific binding of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein. Some surfaces disclosed herein exhibit a ratio of specific to nonspecific fluorescence of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein.

As noted, in some instances, the degree of non-specific binding exhibited by the disclosed low-binding supports may be assessed using a standardized protocol for contacting the surface with a labeled protein (e.g., bovine serum albumin (BSA), streptavidin, a DNA polymerase, a reverse transcriptase, a helicase, a single-stranded binding protein (SSB), etc., or any combination thereof), a labeled nucleotide, a labeled oligonucleotide, etc., under a standardized set of incubation and rinse conditions, followed be detection of the amount of label remaining on the surface and comparison of the signal resulting therefrom to an appropriate calibration standard. In some instances, the label may comprise a fluorescent label. In some instances, the label may comprise a radioisotope. In some instances, the label may comprise any other detectable label known to one of skill in the art. In some instances, the degree of non-specific binding exhibited by a given support surface formulation may thus be assessed in terms of the number of non-specifically bound protein molecules (or other molecules) per unit area. In some instances, the low-binding supports of the present disclosure may exhibit non-specific protein binding (or non-specific binding of other specified molecules, (e.g., cyanins such as Cy3, or Cy5, etc., fluoresceins, coumarins, rhodamines, etc. or other dyes disclosed herein)) of less than 0.001 molecule per $\mu m^2$, less than 0.01 molecule per $\mu m^2$, less than 0.1 molecule per $\mu m^2$, less than 0.25 molecule per $\mu m^2$, less than 0.5 molecule per $\mu m^2$, less than 1 molecule per $\mu m^2$, less than 10 molecules per $\mu m^2$, less than 100 molecules per $\mu m^2$, or less than 1,000 molecules per $\mu m^2$. Those of skill in the art will realize that a given support surface of the present disclosure may exhibit non-specific binding falling anywhere within this range, for example, of less than 86 molecules per $\mu m^2$. For example, some modified surfaces disclosed herein exhibit nonspecific protein binding of less than 0.5 molecule/$\mu m^2$ following contact with a 1 $\mu M$ solution of Cy3 labeled streptavidin (GE Amersham) in phosphate buffered saline (PBS) buffer for 15 minutes, followed by 3 rinses with deionized water. Some modified surfaces disclosed herein exhibit nonspecific binding of Cy3 dye molecules of less than 0.25 molecules per $\mu m^2$. In independent nonspecific binding assays, 1 µM labeled Cy3 SA (ThermoFisher), 1 µM Cy5 SA dye (ThermoFisher), 10 µM Aminoallyl-dUTP-ATTO-647N (Jena Biosciences), 10 µM Aminoallyl-dUTP-ATTO-Rho1 1 (Jena Biosciences), 10 µM Aminoallyl-dUTP-ATTO-Rho1 1 (Jena Biosciences), 10 µM 7-Propargylamino-7-deaza-dGTP-Cy5 (Jena Biosciences, and 10 µM 7-Propargylamino-7-deaza-dGTP-Cy3 (Jena Biosciences) were incubated on the low binding substrates at 37° C. for 15 minutes in a 384 well plate format. Each well was rinsed 2-3× with 50 ul deionized RNase/DNase Free water and 2-3× with 25 mM ACES buffer pH 7.4. The 384 well plates were imaged on a GE Typhoon instrument using the Cy3, AF555, or Cy5 filter sets (according to dye test performed) as specified by the manufacturer at a PMT gain setting of 800 and resolution of 50-100 µm. For higher resolution imaging, images were collected on an Olympus IX83 microscope (Olympus Corp., Center Valley, Pa.) with a total internal reflectance fluorescence (TIRF) objective (100×, 1.5 NA, Olympus), a CCD camera (e.g., an Olympus EM-CCD monochrome camera, Olympus XM-10 monochrome camera, or an Olympus DP80 color and monochrome camera), an illumination source (e.g., an Olympus 100W Hg lamp, an Olympus 75W Xe lamp, or an Olympus U-HGLGPS fluorescence light source), and excitation wavelengths of 532 nm or 635 nm. Dichroic mirrors were purchased from Semrock (IDEX Health & Science, LLC, Rochester, N.Y.), e.g., 405, 488, 532, or 633 nm dichroic reflectors/beamsplitters, and band pass filters were chosen as 532 LP or 645 LP concordant with the appropriate excitation wavelength. Some modified surfaces disclosed herein exhibit nonspecific binding of dye molecules of less than 0.25 molecules per $\mu m^2$.

In some instances, the surfaces disclosed herein exhibit a ratio of specific to nonspecific binding of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein. In some instances, the surfaces disclosed herein exhibit a ratio of specific to nonspecific fluorescence signals for a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein.

The low-background surfaces consistent with the disclosure herein may exhibit specific dye attachment (e.g., Cy3 attachment) to non-specific dye adsorption (e.g., Cy3 dye adsorption) ratios of at least 4:1, 5:1, 6:1, 7:1, 8:1, 9:1, 10:1, 15:1, 20:1, 30:1, 40:1, 50:1, or more than 50 specific dye molecules attached per molecule nonspecifically adsorbed. Similarly, when subjected to an excitation energy, low-background surfaces consistent with the disclosure herein to which fluorophores, e.g., Cy3, have been attached may exhibit ratios of specific fluorescence signal (e.g., arising from Cy3-labeled oligonucleotides attached to the surface) to non-specific adsorbed dye fluorescence signals of at least 4:1, 5:1, 6:1, 7:1, 8:1, 9:1, 10:1, 15:1, 20:1, 30:1, 40:1, 50:1, or more than 50:1.

In some instances, the degree of hydrophilicity (or "wettability" with aqueous solutions) of the disclosed support surfaces may be assessed, for example, through the measurement of water contact angles in which a small droplet of water is placed on the surface and its angle of contact with the surface is measured using, e.g., an optical tensiometer. In some instances, a static contact angle may be determined. In some instances, an advancing or receding contact angle may be determined. In some instances, the water contact angle for the hydrophilic, low-binding support surfaced disclosed herein may range from about 0 degrees to about 30 degrees. In some instances, the water contact angle for the hydrophilic, low-binding support surfaced disclosed herein may no more than 50 degrees, 40 degrees, 30 degrees, 25 degrees, 20 degrees, 18 degrees, 16 degrees, 14 degrees, 12 degrees, 10 degrees, 8 degrees, 6 degrees, 4 degrees, 2 degrees, or 1 degree. In many cases the contact angle is no more than 40 degrees. Those of skill in the art will realize that a given hydrophilic, low-binding support surface of the present disclosure may exhibit a water contact angle having a value of anywhere within this range.

In some instances, the hydrophilic surfaces disclosed herein facilitate reduced wash times for bioassays, often due to reduced nonspecific binding of biomolecules to the low-binding surfaces. In some instances, adequate wash steps may be performed in less than 60, 50, 40, 30, 20, 15, 10, or less than 10 seconds. For example, in some instances adequate wash steps may be performed in less than 30 seconds.

Some low-binding surfaces of the present disclosure exhibit significant improvement in stability or durability to prolonged exposure to solvents and elevated temperatures, or to repeated cycles of solvent exposure or changes in temperature. For example, in some instances, the stability of the disclosed surfaces may be tested by fluorescently labeling a functional group on the surface, or a tethered biomolecule (e.g., an oligonucleotide primer) on the surface, and monitoring fluorescence signal before, during, and after prolonged exposure to solvents and elevated temperatures, or to repeated cycles of solvent exposure or changes in temperature. In some instances, the degree of change in the fluorescence used to assess the quality of the surface may be less than 1%, 2%, 3%, 4%, 5%, 10%, 15%, 20%, or 25% over a time period of 1 minute, 2 minutes, 3 minutes, 4 minutes, 5 minutes, 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 15 hours, 20 hours, 25 hours, 30 hours, 35 hours, 40 hours, 45 hours, 50 hours, or 100 hours of exposure to solvents and/or elevated temperatures (or any combination of these percentages as measured over these time periods). In some instances, the degree of change in the fluorescence used to assess the quality of the surface may be less than 1%, 2%, 3%, 4%, 5%, 10%, 15%, 20%, or 25% over 5 cycles, 10 cycles, 20 cycles, 30 cycles, 40 cycles, 50 cycles, 60 cycles, 70 cycles, 80 cycles, 90 cycles, 100 cycles, 200 cycles, 300 cycles, 400 cycles, 500 cycles, 600 cycles, 700 cycles, 800 cycles, 900 cycles, or 1,000 cycles of repeated exposure to solvent changes and/or changes in temperature (or any combination of these percentages as measured over this range of cycles).

In some instances, the surfaces disclosed herein may exhibit a high ratio of specific signal to nonspecific signal or other background. For example, when used for nucleic acid amplification, some surfaces may exhibit an amplification signal that is at least 4, 5, 6, 7, 8, 9, 10, 15, 20, 30, 40, 50, 75, 100, or greater than 100 fold greater than a signal of an adjacent unpopulated region of the surface. Similarly, some surfaces exhibit an amplification signal that is at least 4, 5, 6, 7, 8, 9, 10, 15, 20, 30, 40, 50, 75, 100, or greater than 100 fold greater than a signal of an adjacent amplified nucleic acid population region of the surface.

In some instances, fluorescence images of the disclosed low background surfaces when used in nucleic acid hybridization or amplification applications to create clusters of hybridized or clonally-amplified nucleic acid molecules (e.g., that have been directly or indirectly labeled with a fluorophore) exhibit contrast-to-noise ratios (CNRs) of at least 10, 20, 30, 40, 50, 60, 70, 80, 90, 100, 110, 120, 130, 140, 150, 160, 170, 180, 190, 20, 210, 220, 230, 240, 250, or greater than 250.

One or more types of primer may be attached or tethered to the support surface. In some instances, the one or more types of adapters or primers may comprise spacer sequences, adapter sequences for hybridization to adapter-ligated target library nucleic acid sequences, forward amplification primers, reverse amplification primers, sequencing primers, and/or molecular barcoding sequences, or any combination thereof. In some instances, 1 primer or adapter sequence may be tethered to at least one layer of the surface. In some instances, at least 2, 3, 4, 5, 6, 7, 8, 9, 10, or more than 10 different primer or adapter sequences may be tethered to at least one layer of the surface.

In some instances, the tethered adapter and/or primer sequences may range in length from about 10 nucleotides to about 100 nucleotides. In some instances, the tethered adapter and/or primer sequences may be at least 10, at least 20, at least 30, at least 40, at least 50, at least 60, at least 70, at least 80, at least 90, or at least 100 nucleotides in length. In some instances, the tethered adapter and/or primer sequences may be at most 100, at most 90, at most 80, at most 70, at most 60, at most 50, at most 40, at most 30, at most 20, or at most 10 nucleotides in length. Any of the lower and upper values described in this paragraph may be combined to form a range included within the present disclosure, for example, in some instances the length of the tethered adapter and/or primer sequences may range from about 20 nucleotides to about 80 nucleotides. Those of skill in the art will recognize that the length of the tethered adapter and/or primer sequences may have any value within this range, e.g., about 24 nucleotides.

In some instances, the resultant surface density of primers on the low binding support surfaces of the present disclosure may range from about 100 primer molecules per $\mu m^2$ to about 100,000 primer molecules per $\mu m^2$. In some instances, the resultant surface density of primers on the low binding support surfaces of the present disclosure may range from about 1,000 primer molecules per $\mu m^2$ to about 1,000,000 primer molecules per $\mu m^2$. In some instances, the surface density of primers may be at least 1,000, at least 10,000, at least 100,000, or at least 1,000,000 molecules per $\mu m^2$. In some instances, the surface density of primers may be at most 1,000,000, at most 100,000, at most 10,000, or at most 1,000 molecules per $\mu m^2$. Any of the lower and upper values described in this paragraph may be combined to form a range included within the present disclosure, for example, in some instances the surface density of primers may range from about 10,000 molecules per $\mu m^2$ to about 100,000 molecules per $\mu m^2$. Those of skill in the art will recognize that the surface density of primer molecules may have any value within this range, e.g., about 455,000 molecules per $\mu m^2$. In some instances, the surface density of target library nucleic acid sequences initially hybridized to adapter or primer sequences on the support surface may be less than or equal to that indicated for the surface density of tethered primers. In some instances, the surface density of clonally-amplified target library nucleic acid sequences hybridized to adapter or primer sequences on the support surface may span the same range as that indicated for the surface density of tethered primers.

Local densities as listed above do not preclude variation in density across a surface, such that a surface may comprise a region having an oligo density of, for example, 500,000/$\mu m^2$, while also comprising at least a second region having a substantially different local density.

VI. Illustrative Alternative Embodiments

The disclosed methods of determining the sequence of a target nucleic acid comprise: a) contacting a double-stranded or partially double-stranded target nucleic acid molecule comprising the template strand to be sequenced and a primer strand to be elongated with one or more of the disclosed nucleic acid binding compositions; and b) detecting the binding of a nucleic acid binding composition to the nucleic acid molecule, thereby determining the presence of one of said one or more nucleic acid binding compositions on said nucleic acid molecule and the identity of the next nucleotide (i.e., the N+1 or terminal nucleotide) to be incorporated into the complementary strand.

The sequencing method may further comprise incorporating the N+1 or terminal nucleotide into the primer strand, and then repeating the contacting, detecting, and incorporating steps for one or more additional iterations, thereby determining the sequence of the template strand of the nucleic acid molecule. After the step of detecting the ternary binding complex, the primed strand of the primed target nucleic acid is extended for one base before another round of analysis is performed. The primed target nucleic acid can be extended using the conjugated nucleotide that is attached to the polymer in the multivalent binding composition, or using an unconjugated or untethered free nucleotide that is provided after the multivalent binding composition has been removed.

The extension of the primed target nucleic acid may be prevented or inhibited due to a blocked nucleotide on the strand or the use of polymerase that is catalytically inactive. When the nucleotide in the polymer-nucleotide conjugate has a blocking group that prevents the extension of the nucleic acid, incorporation of a nucleotide may be achieved by the removal of a blocking group from said nucleotide (such as by detachment of said nucleotide from its polymer, branched polymer, dendrimer, particle, or the like). When the extension of the primed target nucleic acid is inhibited due to the use of polymerase that is catalytically inactive, incorporation of a nucleotide may be achieved by the provision of a cofactor or activator such as a metal ion.

Detection of the ternary complex is achieved prior to, concurrently with, or following the incorporation of the nucleotide residue. In some embodiments, a primed target nucleic acid may comprise a target nucleic acid with multiple primed locations for the attachment of polymerases and/or nucleic acid binding moieties. In some embodiments, multiple polymerases may be attached to a single target nucleic acid molecule, such as at multiple sites within a target nucleic acid molecule. In some embodiments, multiple polymerases may be bound to a multivalent binding composition disclosed herein comprising multiple nucleotides. In some embodiments, a target nucleic acid molecule may be a product of a strand displacement synthesis, a rolling circle amplification, a concatenation or fusion of multiple copies of a query sequence, or other such methods as are known in the art or as are disclosed elsewhere herein to produce nucleic acid molecules comprising multiple copies of an identical sequence. Therefore, in some embodiments, multiple polymerases may be attached at multiple identical or substantially identical locations within a target nucleic acid which comprises multiple identical or substantially identical copies of a query sequence. In some embodiments, said multiple polymerases may then be involved in interactions with one or more multivalent binding complexes; however, in preferred embodiments, the number of binding sites within a target nucleic acid is at least two, and the number of nucleotides or substrate moieties present on a particle-nucleotide conjugate such as a polymer-nucleotide conjugate is also greater than or equal to two.

It may be advantageous to provide the multivalent binding compositions in combination with other elements such as to provide optimized signals, for example to provide identification of a nucleotide at a particular position in a nucleic acid sequence. In some embodiments, the compositions disclosed herein are provided in combination with a surface providing low background binding or low levels of protein binding, especially a hydrophilic or polymer coated surface. Representative surfaces may be found, for example, in U.S. patent application Ser. No. 16/363,842, the contents of which are hereby incorporated by reference in their entirety.

In some instances, the nucleic acid molecule is tethered to the surface of a solid support, e.g., through hybridization of the template strand to an adapter nucleic acid sequence or primer nucleic acid sequence that is tethered to the solid support. In some instances, the solid support comprises a glass, fused-silica, silicon, or polymer substrate. In some instances, the solid support comprises a low non-specific binding coating comprising one or more hydrophilic polymer layers (e.g. PEG layers) where at least one of the hydrophilic polymer layers comprises a branched polymer molecule (e.g., a branched PEG molecule comprising 4, 8, 16, or 32 branches).

The solid support comprises oligonucleotide adapters or primers tethered to at least one hydrophilic polymer layer at a surface density ranging from about 1,000 primer molecules per $\mu m^2$ to about 1,000,000 primer molecules per $\mu m^2$. In some instances, the surface density of oligonucleotide primers may be at least 1,000, at least 10,000, at least 100,000, or at least 1,000,000 molecules per $\mu m^2$. In some instances, the surface density of oligonucleotide primers may be at most 1,000,000, at most 100,000, at most 10,000, or at most 1,000 molecules per $\mu m^2$. Any of the lower and upper values described in this paragraph may be combined to form a range included within the present disclosure, for example, in some instances the surface density of primers may range from about 10,000 molecules per $\mu m^2$ to about 100,000 molecules per $\mu m^2$. Those of skill in the art will recognize that the surface density of primer molecules may have any value within this range, e.g., about 455,000 molecules per $\mu m^2$.

One of ordinary skill would recognize that in a series of iterative sequencing reactions, occasionally one or more sites will fail to incorporate a nucleotide during a given cycle, thus leading one or more sites to be unsynchronized with the bulk of the elongating nucleic acid chains. Under conditions in which sequencing signals are derived from reactions occurring on single copies of a target nucleic acid, these failures to incorporate will yield discrete errors in the output sequence. It is an object of the present disclosure to describe methods for reducing this type of error in sequencing reactions. For example, the use of multivalent substrates that are capable of incorporation into the elongating strand, by providing increased probabilities of rebinding upon premature dissociation of a ternary polymerase complex, can reduce the frequency of "skipped" cycles in which a base is not incorporated. Thus, in some embodiments, the present disclosure contemplates the use of multivalent substrates as disclosed herein in which the nucleoside moiety is comprised within a nucleotide having a free, or reversibly modified, 5' phosphate, diphosphate, or triphosphate moiety, and wherein the nucleotide is connected to the particle or polymer as disclosed herein, through a labile or cleavable linkage. In some embodiments, the present disclosure contemplates a reduction in the intrinsic error rate due to skipped incorporations as a result of the use of the multivalent substrates disclosed herein.

The present disclosure also contemplates sequencing reactions in which sequencing signals from or relating to a given sequence are derived from or originate within definable regions containing multiple copies of the target sequence. Sequencing methods incorporating multiple copies of a target sequence have the advantage that signals can be amplified due to the presence of multiple simultaneous sequencing reactions within the defined region, each providing its own signal. The presence of multiple signals within a defined area also reduces the impact of any single skipped cycle, due to the fact that the signal from a large number of correct base calls can overwhelm the signal from a smaller number of skipped or incorrect base calls. The present disclosure further contemplates the inclusion of free, unlabeled nucleotides during elongation reactions, or during a separate part of the elongation cycle, in order to provide incorporation at sites that may have been skipped in previous cycles. For example, during or following an incorporation cycle, unlabeled blocked nucleotides may be added such that they may be incorporated at skipped sites. The unlabeled blocked nucleotides may be of the same type or types as the nucleotide attached to the multivalent binding substrate or substrates that are or were present during a particular cycle, or a mixture of 1, 2, 3, 4 or more types of unlabeled blocked nucleotides may be included.

When each sequencing cycle proceeds perfectly, each reaction within the defined region will provide an identical signal. However, as noted elsewhere herein, in a series of iterative sequencing reactions, occasionally one or more sites will fail to incorporate a nucleotide during a given cycle, thus leading one or more sites to be unsynchronized with the bulk of the elongating nucleic acid chains. This issue, referred to as "phasing," leads to degradation of the sequencing signal as the signal is contaminated with spurious signals from sites having skipped one or more cycles. This, in turn, creates the potential for errors in base identification. The progressive accumulation of skipped cycles through multiple cycles also reduces the effective read length, due to progressive degradation of the sequencing signal with each cycle. It is a further object of this disclosure to provide methods for reducing phasing errors and/or to improve read length in sequencing reactions.

The sequencing method can include contacting a target nucleic acid or multiple target nucleic acids, comprising multiple linked or unlinked copies of a target sequence, with the multivalent binding compositions described herein. Contacting said target nucleic acid, or multiple target nucleic acids comprising multiple linked or unlinked copies of a target sequence, with one or more particle-nucleotide conjugates may provide a substantially increased local concentration of the correct nucleotide being interrogated in a given sequencing cycle, thus suppressing signals from improper incorporations or phased nucleic acid chains (i.e., those elongating nucleic acid chains which have had one or more skipped cycles).

Methods of obtaining nucleic acid sequence information can include contacting a target nucleic acid, or multiple target nucleic acids, wherein said target nucleic acid or multiple target nucleic acids comprise multiple linked or unlinked copies of a target sequence, with one or more particle-nucleotide conjugates. This method results in a reduction in the error rate of sequencing as indicated by reduction in the misidentification of bases, the reporting of nonexistent bases, or the failure to report correct bases. In some embodiments, said reduction in the error orate of sequencing may comprise a reduction of 5%, 10%, 15%, 20% 25%, 50%, 75%, 100%, 150%, 200%, or more compared to the error rate observed using monovalent ligands, including free nucleotides, labeled free nucleotides, protein or peptide bound nucleotides, or labeled protein or peptide bound nucleotides.

The method of obtaining nucleic acid sequence information can include contacting a target nucleic acid, or multiple target nucleic acids, wherein said templet nucleic acid or multiple target nucleic acids comprise multiple linked or unlinked copies of a target sequence, with one or more particle-nucleotide conjugates. This method results in an increase in average read length of 5%, 10%, 15%, 20% 25%, 50%, 75%, 100%, 150%, 200%, 300%, or more compared to the average read length observed using monovalent ligands, including free nucleotides, labeled free nucleotides, protein or peptide bound nucleotides, or labeled protein or peptide bound nucleotides.

Methods of obtaining nucleic acid sequence information, said methods comprising contacting a target nucleic acid, or multiple target nucleic acids, wherein said target nucleic acid or multiple target nucleic acids comprise multiple linked or unlinked copies of a target sequence, with one or more particle-nucleotide conjugates. This method results in an increase in average read length of 10NT, 20NT, 25NT, 30NT, 50NT, 75NT, 100NT, 125NT, 150NT, 200NT, 250NT, 300NT, 350NT, 400NT, 500NT, or more compared to the average read length observed using monovalent ligands, including free nucleotides, labeled free nucleotides, protein or peptide bound nucleotides, or labeled protein or peptide bound nucleotides.

The use of multivalent binding composition for sequencing effectively shortens the sequencing time. The sequencing reaction cycle comprising the contacting, detecting, and incorporating steps is performed in a total time ranging from about 5 minutes to about 60 minutes. In some instances, the sequencing reaction cycle is performed in at least 5 minutes, at least 10 minutes, at least 20 minutes, at least 30 minutes, at least 40 minutes, at least 50 minutes, or at least 60 minutes. In some instances, the sequencing reaction cycle is performed in at most 60 minutes, at most 50 minutes, at most 40 minutes, at most 30 minutes, at most 20 minutes, at most 10 minutes, or at most 5 minutes. Any of the lower and upper values described in this paragraph may be combined to form a range included within the present disclosure, for example, in some instances the sequencing reaction cycle may be performed in a total time ranging from about 10 minutes to about 30 minutes. Those of skill in the art will recognize that the sequencing cycle time may have any value within this range, e.g., about 16 minutes.

The use of multivalent binding composition for sequencing provides an more accuracy base readout. The disclosed compositions and methods for nucleic acid sequencing will provide an average Q-score for base-calling accuracy over a sequencing run that ranges from about 20 to about 50. In some instances, the average Q-score is at least 20, at least 25, at least 30, at least 35, at least 40, at least 45, or at least 50. Those of skill in the art will recognize that the average Q-score may have any value within this range, e.g., about 32.

In some instances, the disclosed compositions and methods for nucleic acid sequencing will provide a Q-score of greater than 30 for at least 50%, at least 60%, at least 70%, at least 80%, at least 85%, at least 90%, at least 95%, at least 98%, or at least 99% of the terminal (or N+1) nucleotides identified. In some instances, the disclosed compositions and methods for nucleic acid sequencing will provide a Q-score of greater than 35 for at least 50%, at least 60%, at least 70%, at least 80%, at least 85%, at least 90%, at least 95%, at least 98%, or at least 99% of the terminal (or N+1) nucleotides identified. In some instances, the disclosed compositions and methods for nucleic acid sequencing will provide a Q-score of greater than 40 for at least 50%, at least 60%, at least 70%, at least 80%, at least 85%, at least 90%, at least 95%, at least 98%, or at least 99% of the terminal (or N+1) nucleotides identified. In some instances, the disclosed compositions and methods for nucleic acid sequencing will provide a Q-score of greater than 45 for at least 50%, at least 60%, at least 70%, at least 80%, at least 85%, at least 90%, at least 95%, at least 98%, or at least 99% of the terminal (or N+1) nucleotides identified. In some instances, the disclosed compositions and methods for nucleic acid sequencing will provide a Q-score of greater than 50 for at least 50%, at least 60%, at least 70%, at least 80%, at least 85%, at least 90%, at least 95%, at least 98%, or at least 99% of the terminal (or N+1) nucleotides identified.

The disclosed low non-specific binding supports and associated nucleic acid hybridization and amplification methods may be used for the analysis of nucleic acid molecules derived from any of a variety of different cell, tissue, or sample types known to those of skill in the art. For example, nucleic acids may be extracted from cells, or tissue samples comprising one or more types of cells, derived from eukaryotes (such as animals, plants, fungi, protista), archaebacteria, or eubacteria. In some cases, nucleic acids may be extracted from prokaryotic or eukaryotic cells, such as adherent or non-adherent eukaryotic cells. Nucleic acids are variously extracted from, for example, primary or immortalized rodent, porcine, feline, canine, bovine, equine, primate, or human cell lines. Nucleic acids may be extracted from any of a variety of different cell, organ, or tissue types (e.g., white blood cells, red blood cells, platelets, epithelial cells, endothelial cells, neurons, glial cells, astrocytes, fibroblasts, skeletal muscle cells, smooth muscle cells, gametes, or cells from the heart, lungs, brain, liver, kidney, spleen, pancreas, thymus, bladder, stomach, colon, or small intestine). Nucleic acids may be extracted from normal or healthy cells. Alternately or in combination, acids are extracted from diseased cells, such as cancerous cells, or from pathogenic cells that are infecting a host. Some nucleic acids may be extracted from a distinct subset of cell types, e.g., immune cells (such as T cells, cytotoxic (killer) T cells, helper T cells, alpha beta T cells, gamma delta T cells, T cell progenitors, B cells, B-cell progenitors, lymphoid stem cells, myeloid progenitor cells, lymphocytes, granulocytes, Natural Killer cells, plasma cells, memory cells, neutrophils, eosinophils, basophils, mast cells, monocytes, dendritic cells, and/or macrophages, or any combination thereof), undifferentiated human stem cells, human stem cells that have been induced to differentiate, rare cells (e.g., circulating tumor cells (CTCs), circulating epithelial cells, circulating endothelial cells, circulating endometrial cells, bone marrow cells, progenitor cells, foam cells, mesenchymal cells, or trophoblasts). Other cells are contemplated and consistent with the disclosure herein.

Nucleic acid extraction from cells or other biological samples may be performed using any of a number of techniques known to those of skill in the art. For example, a typical DNA extraction procedure comprises (i) collection of the cell sample or tissue sample from which DNA is to be extracted, (ii) disruption of cell membranes (i.e., cell lysis) to release DNA and other cytoplasmic components, (iii) treatment of the lysed sample with a concentrated salt solution to precipitate proteins, lipids, and RNA, followed by centrifugation to separate out the precipitated proteins, lipids, and RNA, and (iv) purification of DNA from the supernatant to remove detergents, proteins, salts, or other reagents used during the cell membrane lysis step.

A variety of suitable commercial nucleic acid extraction and purification kits are consistent with the disclosure herein. Examples include, but are not limited to, the QIAamp® kits (for isolation of genomic DNA from human samples) and DNAeasy kits (for isolation of genomic DNA from animal or plant samples) from Qiagen (Germantown, Md.), or the Maxwell® and ReliaPrep™ series of kits from Promega (Madison, Wis.).

VII. Examples

1. Preparation of Multivalent Binding Composition

One type of multi-armed substrate, as shown in FIG. 5A were made by reacting propargylamine dNTPs with Biotin-PEG-NHS. This aqueous reaction was driven to completion and purified; resulting in a pure Biotin-PEG-dNTP species. In separate reactions, several different PEG lengths were used, varying from 1K to 20K. The Biotin-PEG-dNTP species were mixed with either freshly prepared or commercially sourced dye-labeled streptavidin using a Dye:SA ratio of 3-5:1. Mixing of Biotin-PEG-dNTP with dye-labeled streptavidin was done in the presence of excess biotin-PEG-dNTP to ensure saturation of the biotin binding sites on each streptavidin tetramer. Complete complexes were purified away from excess biotin-PEG-dNTP by size exclusion chromatography. Each nucleotide type was conjugated and purified separately, then mixed together to create a 4 base mix for sequencing.

Another type of multi-armed substrate as shown in FIG. 5A was made in a single pot by reacting multiarm PEG NHS with excess Dye-NH2 and propargylamine dNTPs. Various multiarm PEG NHS variants were used ranging from 4-16 arms and ranging in molecular weight from 5K to 40K. After reacting, excess small molecule dye and dNTP were removed by size exclusion chromatography. Each nucleotide type was conjugated and purified independently then mixed together to create a 4 base mix for sequencing.

Class II substrates as shown in FIG. 5B were made using 1 pot reactions to simultaneously conjugate dye and dNTP. Alkyne-PEG-NHS was reacted with excess propargylamine dNTP. This product (Alkyne-PEG-dNTP) was then purified to homogeneity by chromatography. Multiple PEG lengths were used, varying between 1K and 20K. Dendrimer cores containing a variable, discrete number (12, 24, 48, 96) of azide conjugation sites. Conjugation of Alkyne-Dye and Alkyne-PEG-dNTP to the dendrimer core occurred in a one pot reaction containing excess dye and dNTP species via copper mediated click chemistry. After reacting, excess small molecule dye and dNTP were removed by size exclusion chromatography. Each nucleotide type was conjugated and purified independently then mixed together to create a 4 base mix for sequencing. We note that this scheme allows the ready substitution of alternative cores, such as dextrans, other polymers, proteins, etc.

Class III polymer-nucleotide conjugates as shown in FIG. 5C were constructed by reacting 4- or 8-arm PEG NHS with a saturating mixture of biotin and propargylamine dNTP. This reaction was then purified by size exclusion chromatography. The result of this reaction was a multiarm PEG containing a discrete distribution of biotin and nucleotide. This heterogeneous population was then reacted with dye-labeled streptavidin and purified by size exclusion chromatography. Each nucleotide type was conjugated and purified independently then mixed together to create a 4 base mix for sequencing. We note that the distribution of biotin and nucleotide is tunable by the input ration of Biotin-NH2 to propargylamine dNTP.

2. Detection of Ternary Complex

Binding reactions using the multivalent binding composition having PEG polymer-nucleotide conjugates were analyzed to detect possible formation of ternary binding complex, and the fluorescence images of the various steps are illustrated in FIGS. 9A-9G. In FIG. 9A, red and green fluorescent images post exposure of DNA rolling circle application (RCA) templates (G and A first base) to 500 nM base labeled nucleotides (A-Cy3 and G-Cy5) in exposure buffer containing 20 nM Klenow polymerase and 2.5 mM Sr+2. Multivalent PEG-substrate compositions were prepared using varying ratios of 4-armed PEG-amine (4Arm-PEG-NH), biotin-PEG-amine (Biotin-PEG-NH), and nucleotide (Nuc) as follows: Samples PB1 and PB5, 4Arm-PEG-NH: Biotin-PEG-NH: Nuc=0.25: 1: 0.5; Sample PB2, 4ArmPEG-NH: Biotin-PEG-NH: Nuc=0.125: 0.5: 0.25; Sample PB3, 4ArmPEG-NH: Biotin-PEG-NH: Nuc=0.25: 1: 0.5. Images were collected after washing with imaging buffer with the same composition as the exposure buffer, but containing no nucleotides or polymerase.

Figure 7G:
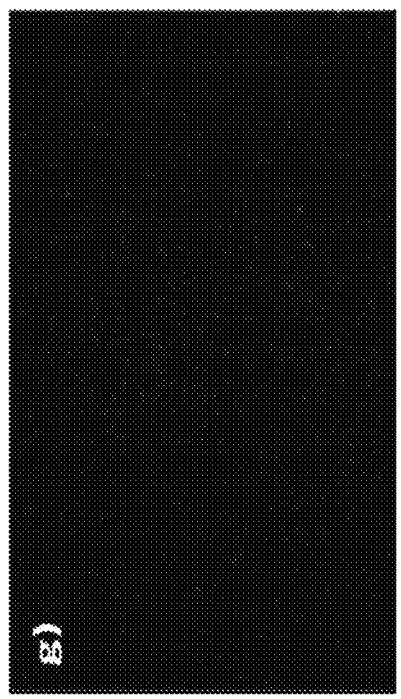

Contrast was scaled to maximize visualization of the dimmest signals, but no signals persisted following washing with imaging buffer (a. inset). In FIGS. 7B-7E, the fluorescence images showing multivalent PEG-nucleotide (base-labeled) ligands at 500 nM after mixing in the exposure buffer and imaging in the imaging buffer as above. (FIG. 9C. PB2; FIG. 9D. PB3; FIG. 9E. PB5). In FIGS. 7G-7I, the fluorescence images showing further base discrimination by exposure of multivalent ligands to inactive mutants of klenow polymerase FIG. 9G. D882H; FIG. 9H. D882E; FIG. 9I. D882A, and the wild type Klenow (control) enzyme is shown in FIG. 9J.

Using multivalent ligands formulations, the base discrimination can be enabled by providing polymerase-ligand interactions having increased avidity. In addition it is shown that increased concentration of multivalent ligands can generate higher signals as well as various Klenow mutations that knock out catalytic activity can be used for avidity-based sequencing.

3. Sequencing of Target Nucleic Acid Based on Ternary Complex

Figure 10A:
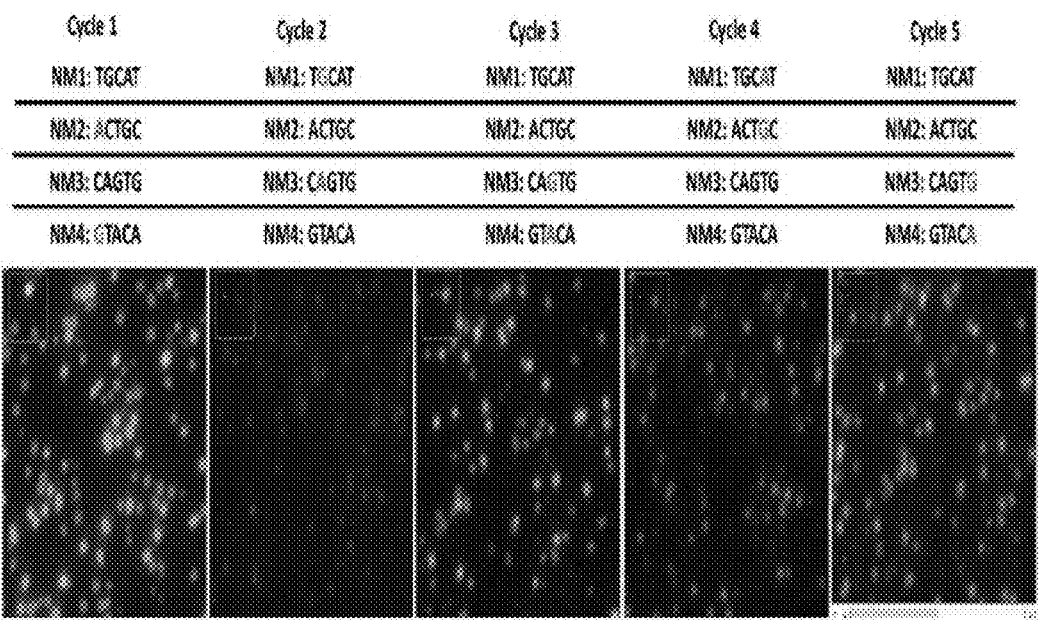
FIGS. 10A-10B show the efficacy of the multivalent reporter compositions in determining the base sequence of a DNA sequence over 5 sequencing cycles.
Figure 10B:
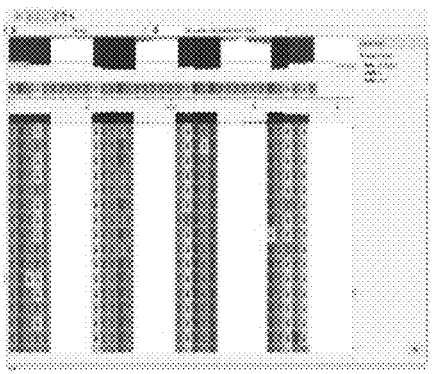

In order to demonstrate sequencing based on multivalent ligand reporters, 4 known templates were amplified using RCA methods on a low binding substrate. Successive cycles were exposed to exposure buffer containing 20 nM Klenow polymerase and 2.5 mM $Sr^{+2}$ and washed with imaging buffer and imaged. After imaging, the substrates were washed with wash buffer (EDTA and high salt) and blocked nucleotides were added to proceed to the next base. The cycle was repeated for 5 cycles. Spots were detected using standard imaging processing and spot detection and the sequences were called using a two color green and red scheme (G-Cy3 and A-Cy5) to identify the templates being cycled. As shown in FIG. 10A and FIG. 10B, multivalent ligands are able to provide base discrimination through all 5 sequencing cycles.

4. Control of Nucleotide Dissociation from Ternary Complex

Ternary complexes are prepared and imaged as in Example 2. The complexes are imaged over varying lengths of time to demonstrate the persistence of the ternary complex, e.g., as long as 60 seconds. After a length of time, the complexes are washed with a buffer identical to the buffer used for the formation of the complexes, only lacking any divalent cation, e.g., 10 mM Tris pH 8.0, 0.5 mM EDTA, 50 mM NaCl, 0.016% Triton X100 (without SrOAc), or, alternatively, the complexes are washed with a buffer identical to the buffer used for the formation of the complexes, which contains a chelating agent but otherwise lacks any divalent cation, e.g., 10 mM Tris pH 8.0, 0.5 mM EDTA, 50 mM NaCl, 0.016% Triton X100 (without SrOAc), with 100 nm-100 mM EDTA. The fluorescence from the complexes is observed over time allowing observation and quantitation of the dissociation of the ternary complexes. A representative time course of this dissolution is shown in FIG. 6.

5. Extension of Target Nucleic Acid Complementary Sequence

After preparing, imaging, and dissociating ternary complexes as in Example 4, a deblocking solution is flowed into the chamber containing the bound DNA molecules, sufficient to remove the blocking moiety, such as an O-azidomethyl group, an O-alkyl hydroxylamino group, or an O-amino group, from the 3' end of the elongating DNA strand. Either following or concurrently with this, an extension solution is flowed into the chamber containing the bound DNA molecules. The extension solution contains a buffer, a divalent cation sufficient to support polymerase activity, an active polymerase, and an appropriate amount of all four nucleotides, where the nucleotides are blocked such that they are incapable of supporting further elongation after the addition of a single nucleotide to the elongating DNA strand, such as by incorporation of a 3'-O-azidomnethyl group, a 3'-O-alkyl hydroxylamino group, or a 3'-O-amino group. The elongating strand is thus extended by one and only one base, and the binding of catalytically inactive polymerase and multivalent binding substrate can be used to call the next base in the cycle.

Alternatively, the nucleotides attached to the multivalent substrate may be attached through a labile bond, such that a buffer may be flowed into the chamber containing the bound DNA molecules containing a divalent cation or other cofactor sufficient to render the polymerase catalytically active. Prior to, after, or concurrently with this, conditions may be provided that are sufficient to cleave the base from the multivalent substrate such that it may be incorporated into the elongating strand. This cleavage and incorporation causes the dissociation of the label and the polymer backbone of the multivalent substrate while extending the elongating DNA strand by exactly one base. Washing to remove used polymer backbone is carried out, and new multivalent substrate is flowed into the chamber containing the bound DNA molecules, allowing the new base to be called as in Example 1.

6. Use of Polymer-Nucleotide Conjugates with Various Lengths of PEG Branch

Figure 8:
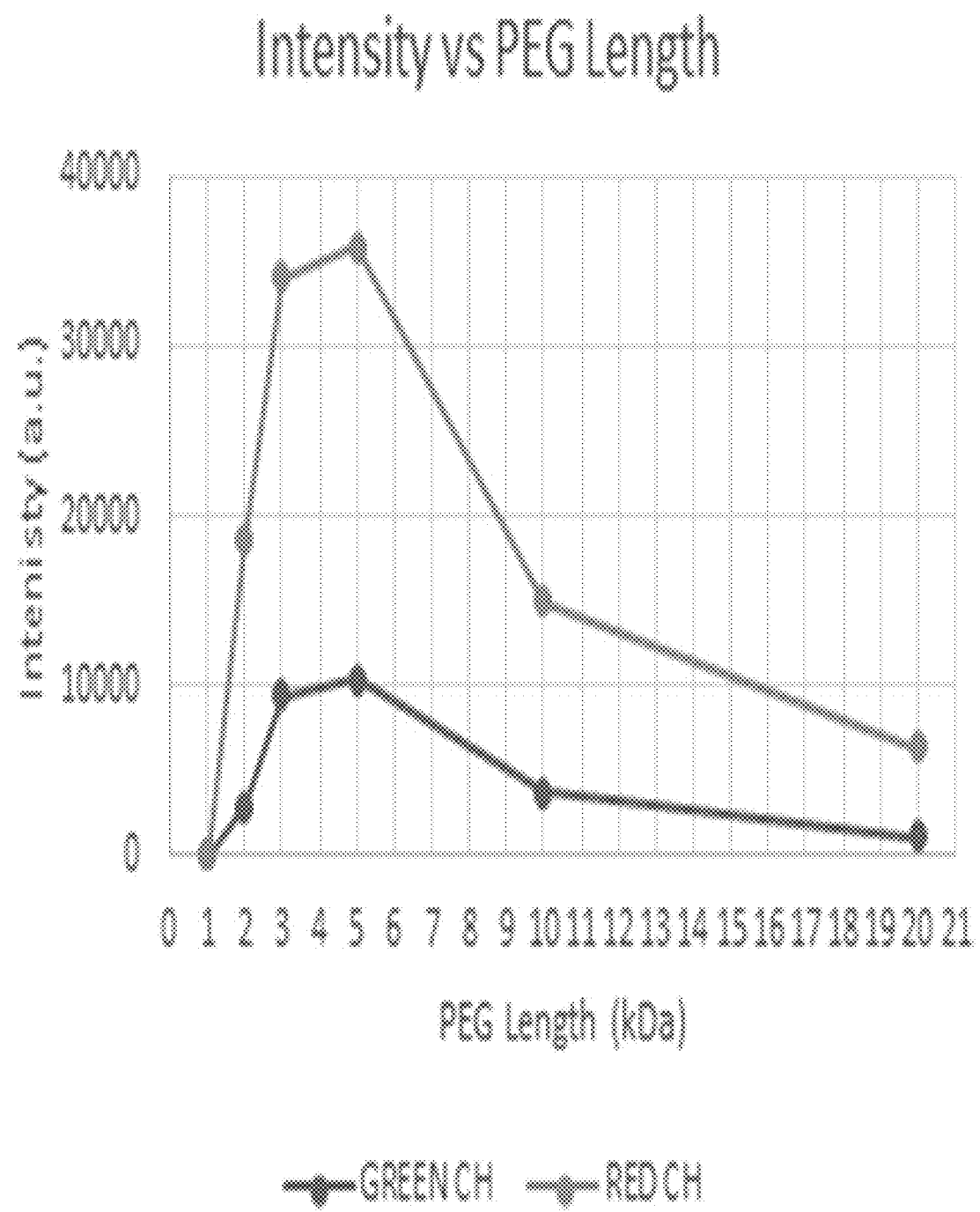
FIG. 8 shows a quantitative representation of the fluorescence intensities in the images shown in FIGS. 7A-7F, separated by color value, with orange trace corresponding to the red label (Cy3 label; A bases) and blue trace corresponding to the green label (Cy5 label; G bases).

The polymer-nucleotide conjugates having varying PEG arm lengths described in Example 3 were subjected to a single sequencing cycle and imaged as described in Example 1. As shown in FIGS. 7A-7G, increasing the length of the PEG branches led to increased signal up to a length corresponding to an apparent average PEG MW of 5K (FIGS. 7A-7D). The use of longer PEG arms than this led to decreases in the fluorescence signal for both Cy3-A and Cy5-G (FIG. 7E-7G). Quantitative measurements of signal intensity are shown graphically in FIG. 8.

7. Enhancement of Multivalent Substrate Binding by Addition of Detergent

Figure 11:
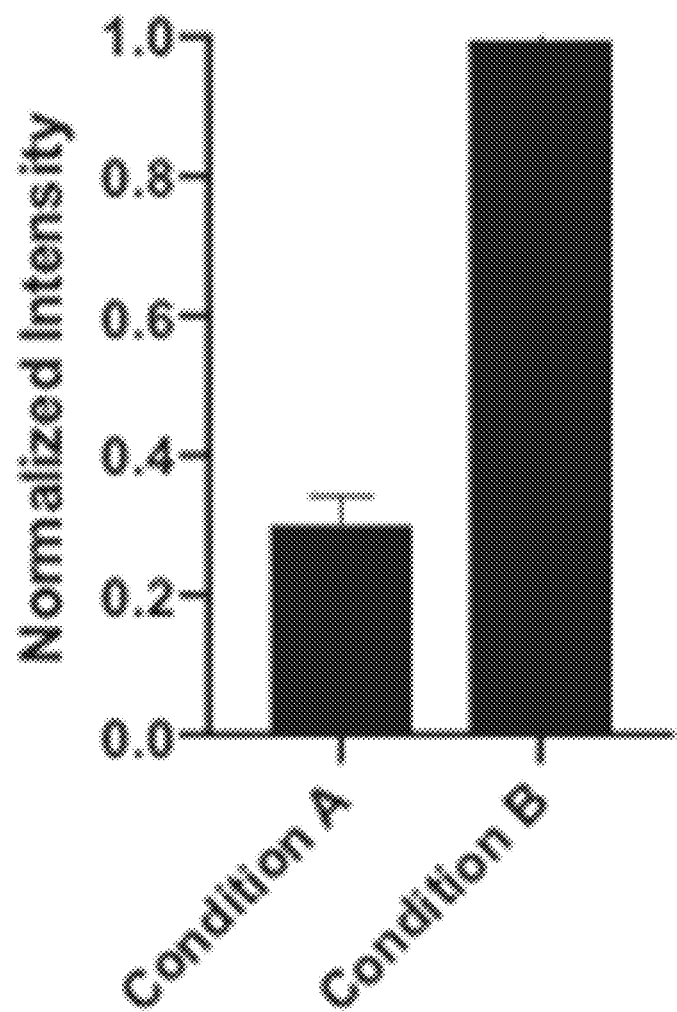
FIG. 11 shows normalized fluorescence from multivalent substrates bound to DNA clusters as in FIG. 9, with the substrate complexes formed in the presence (condition B) and absence (condition A) of Triton-X100 (0.016%).

Multivalent substrates were prepared and assembled into binding complexes in the presence and absence of detergent: one set using 10 mM Tris pH 8.0, 0.5 mM EDTA, 50 mM NaCl, 5 mM SroAc, 0% TritonX100 (Condition A), and one set using 10 mM Tris pH 8.0, 0.5 mM EDTA, 50 mM NaCl, 5 mM SroAc, 0.016% Triton X100. FIG. 11 shows normalized fluorescence from these multivalent substrates bound to DNA clusters, with the substrate complexes formed in the presence (condition B) of Triton-X100 (0.016%) showing clearly enhanced fluorescence intensity.

8. Evaluation of Multivalent Substrate Binding Time Courses

Figure 12:
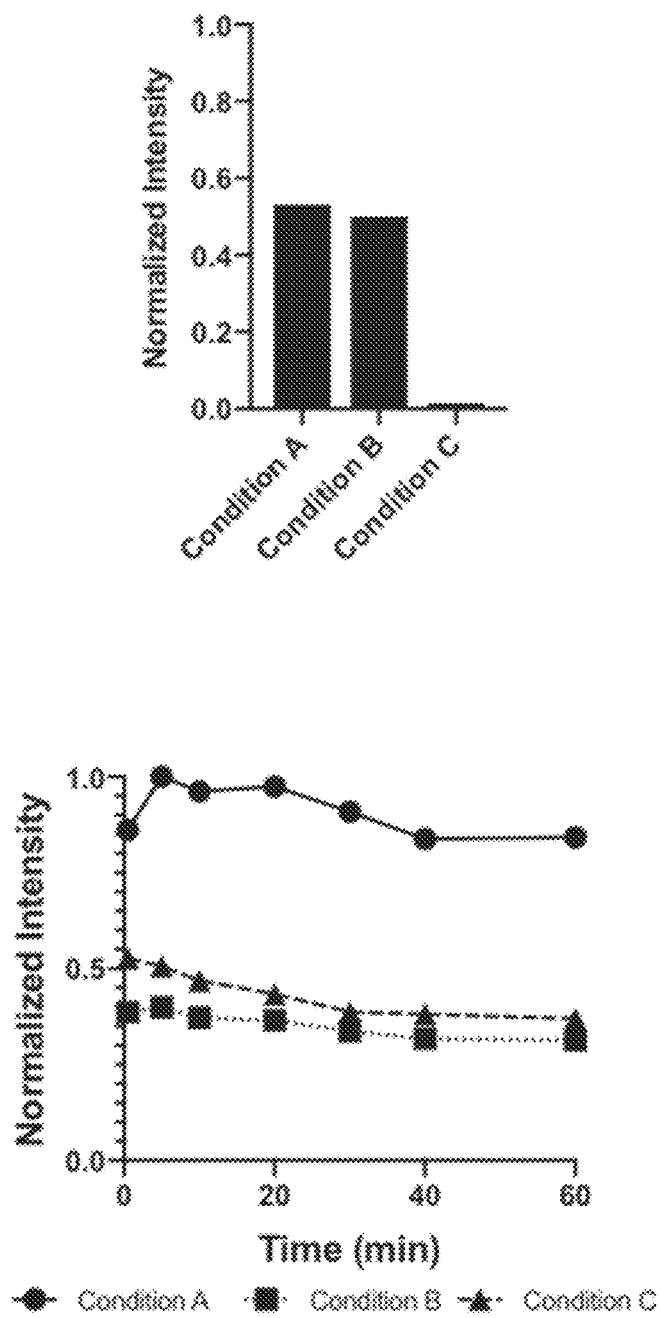
FIG. 12 shows normalized fluorescence of multivalent substrates and free nucleotides. (Top) Two replicates of a multivalent substrate bound to DNA clusters (Conditions A and B) vs. binding complexes formed using labeled free nucleotides (Condition C) after 1 minute; (Bottom) Time course of fluorescence from multivalent substrate complexes over the course of 60 min.

Multivalent substrates were prepared and assembled into binding complexes as in Example 2. Complexes were also formed under identical buffer conditions using free labeled nucleotides. Complexes were imaged over the course of 60 min. to characterize the persistence time of the complexes. FIG. 12 shows representative results. Multivalent binding complexes are stable over timescales of >60 minutes (FIG. 12, bottom) while labeled free nucleotides dissociate in less than one minute (FIG. 12, top).

VIII. Conclusion

The present inventions provide greatly improved methods and compositions for DNA sequencing and biosensor applications. It is to be understood that the above description is intended to be illustrative and not restrictive. Many embodiments will be apparent to those of skill in the art upon reviewing the above description. By way of example, the invention has been described primarily with reference to the use of polymer-nucleotide conjugate, but it will be readily recognized by those of skill in the art that other types of particle-nucleotide conjugates could also be used. For example, in some embodiments it may be desirable to use particle-nucleotide conjugates which include quantum dot; a liposome; or an emulsion particle. Alternatively, the conjugation could be achieved by noncovalent bond such as hydrogen bond or other interactions. The scope of the invention should, therefore, be determined not with reference to the above description, but should instead be determined with reference to the appended claims, along with the full scope of equivalents to which such claims are entitled.

The invention claimed is:

1. A method of determining an identity of a nucleotide in a target nucleic acid sequence, comprising:
    (a) providing a composition comprising:
        (i) two or more copies of said target nucleic acid sequence;
        (ii) two or more primer nucleic acid molecules that are complementary to one or more regions of said target nucleic acid sequence; and
        (iii) two or more polymerase molecules;
    (b) contacting said composition with a polymer-nucleotide conjugate under conditions sufficient to allow a multivalent binding complex to be formed between said polymer-nucleotide conjugate and said two or more copies of said target nucleic acid sequence in said composition of (a), wherein the polymer-nucleotide conjugate comprises two or more nucleotide moieties; and
    (c) detecting said multivalent binding complex, thereby determining the identity of said nucleotide in the target nucleic acid sequence.

2. The method of claim 1, wherein the target nucleic acid sequence is DNA.

3. The method of claim 1, wherein the detection of the binding complex is performed in the absence of unbound or solution-borne polymer nucleotide conjugates.

4. The method of claim 1, wherein the target nucleic acid sequence has been replicated or amplified or has been produced by replication or amplification.

5. The method of claim 1, wherein detecting the multivalent binding complex comprises a fluorescence measurement.

6. The method of claim 1, wherein the contacting comprises use of one type of polymer-nucleotide conjugate.

7. The method of claim 1, wherein the contacting comprises use of two or more types of polymer-nucleotide conjugate.

8. The method of claim 7, wherein each type of the two or more types of polymer-nucleotide conjugate comprises a different type of nucleotide moiety.

9. The method of claim 8, wherein the contacting comprises use of three types of polymer-nucleotide conjugate and wherein each type of the three types of polymer-nucleotide conjugate comprises a different type of nucleotide moiety.

10. The method of claim 1, wherein the polymer-nucleotide conjugate comprises a blocked nucleotide moiety.

11. The method of claim 10, wherein the blocked nucleotide is a 3'-O-azidomethyl, 3'-O-methyl, or 3'-O-alkyl hydroxylamine nucleotide.

12. The method of claim 1, wherein said contacting occurs in the presence of an ion that stabilizes said multivalent binding complex.

13. The method of claim 1, wherein the contacting is done in the presence of strontium ions, magnesium ions, calcium ions, or any combination thereof.

14. The method of claim 1, wherein the polymerase molecules are catalytically inactive.

15. The method of claim 1, wherein the polymerase molecules have been rendered catalytically inactive by mutation or chemical modification.

16. The method of claim 1, wherein the polymerase molecules have been rendered catalytically inactive by the absence of a necessary ion or cofactor.

17. The method of claim 1, wherein the polymerase molecules are catalytically active.

18. The method of claim 1, wherein the polymer-nucleotide conjugate does not comprise a blocked nucleotide moiety.

19. The method of claim 1, wherein the multivalent binding complex has a persistence time of greater than 2 seconds.

20. The method of claim 1, wherein the method is carried out at a temperature within a range of 25° C. to 42° C.

21. The method of claim 1, wherein the polymer-nucleotide conjugate further comprises one or more fluorescent labels and the two or more copies of the target nucleic acid sequence are deposited on, attached to, or hybridized to a surface, wherein a fluorescence image of the multivalent binding complex on the surface has a contrast to noise ratio in the detecting step of greater than 20.

22. The method of claim 1, wherein the composition of (a) is deposited on a surface using a buffer that incorporates a polar aprotic solvent.

23. The method of claim 1, wherein the contacting is performed under a condition that stabilizes said multivalent binding complex when said nucleotide moiety is complementary to a next base of said target nucleic acid sequence and destabilizes said multivalent binding complex when said nucleotide moiety is not complementary to said next base of said target nucleic acid sequence.

24. The method of claim 1, wherein said polymer-nucleotide conjugate comprises a polymer having a plurality of branches and said two or more nucleotide moieties are attached to said branches.

25. The method of claim 24, wherein said first polymer has a star, comb, cross-linked, bottle brush, or dendrimer configuration.

26. The method of claim 1, wherein said polymer-nucleotide conjugate comprises one or more binding groups selected from the group consisting of an avidin, a biotin, an affinity tag, and combinations thereof.

27. The method of claim 1, further comprising a dissociation step that destabilizes said multivalent binding complex formed between the composition of (a) and the polymer-nucleotide conjugate, said dissociation step enabling removal of said polymer-nucleotide conjugate.

28. The method of claim 27, further comprising an extension step to incorporate a nucleotide that is complementary to a next base of the target nucleic acid sequence into said two or more primer nucleic acid molecules.

29. The method of claim 28, wherein the extension step occurs concurrently with or after said dissociation step.

30. The method of claim 1, wherein said polymer-nucleotide conjugate comprises one or more detectable labels.

* * * * *